US006878141B1

(12) United States Patent
Perkins et al.

(10) Patent No.: US 6,878,141 B1
(45) Date of Patent: *Apr. 12, 2005

(54) METHODS SYSTEMS AND KITS FOR LUNG VOLUME REDUCTION

(75) Inventors: Rodney A. Perkins, Woodside, CA (US); Peter P. Soltesz, San Jose, CA (US); Robert Kotmel, Burlingame, CA (US); Anthony D. Wondka, Mountain View, CA (US)

(73) Assignee: Pulmonx, Palo Alto, CA (US)

( * ) Notice: Subject to any disclaimer, the term of this patent is extended or adjusted under 35 U.S.C. 154(b) by 852 days.

This patent is subject to a terminal disclaimer.

(21) Appl. No.: 09/606,320

(22) Filed: Jun. 28, 2000

Related U.S. Application Data

(63) Continuation-in-part of application No. 09/347,032, filed on Jul. 2, 1999, now Pat. No. 6,287,290.

(51) Int. Cl.⁷ .............................................. A61M 31/00
(52) U.S. Cl. ...................................... 604/516; 604/509
(58) Field of Search .............................. 604/28, 35, 43, 604/516, 102.01, 102.02, 101.01, 101.04, 79, 509; 128/207.15, 207.14

(56) References Cited

U.S. PATENT DOCUMENTS

| 3,322,126 A | 5/1967 | Rüusch et al. |
| 3,498,286 A | 3/1970 | Polanyi et al. |
| 3,669,098 A | 6/1972 | Takahashi |

(Continued)

FOREIGN PATENT DOCUMENTS

| WO | WO 92/10971 | 9/1992 |
| WO | WO 95/33506 | 12/1995 |
| WO | WO 98/48706 | 11/1998 |
| WO | WO 98/49191 | 11/1998 |
| WO | WO 99/01076 | 1/1999 |
| WO | WO 99/17827 | 4/1999 |

OTHER PUBLICATIONS

Coryllos and Birnbaum, "Studies in pulmonary gas absorption in bronchial obstruction. I. Two new methods for direct and indirect observation." Amer. J. Med. Sci. (1932) 183:317–326.

Coryllos and Birnbaum, "Studies in pulmonary gas absorption in bronchial obstruction. II. The behavoir and absorption times of oxygen, carbon dioxid, nitrogen, hydrogen, helium, ethylene, nitrous, oxid, ethyl chlorid, and ether in the lung." Amer. J. Med. Sci. (1932) 183:326–347.

Coryllos and Birnbaum, "Studies in pulmonary gas absorption in bronchial obstruction. III. A theory of air absorption in atelectasis." Amer. J. Med. Sci. (1932) 183:347–359.

Becker et al., "Lung volumes before and after lung volume reduction surgery" Am. J. Respir. Crit. Care Med. (1998) 157:1593–1599.

Clark et al., "Lung volume reduction surgery alters management of pulmonary modules in patients with severe COPD" Chest (1997) 112(6):1494–1500.

(Continued)

Primary Examiner—Manuel Mendez
(74) Attorney, Agent, or Firm—Townsend and Townsend and Crew LLP

(57) ABSTRACT

Lung volume reduction is performed in a minimally invasive manner by isolating a lung tissue segment, optionally reducing gas flow obstructions within the segment, and aspirating the segment to cause the segment to at least partially collapse. Further optionally, external pressure may be applied on the segment to assist in complete collapse. Reduction of gas flow obstructions may be achieved in a variety of ways, including over inflation of the lung, introduction of mucolytic or dilation agents, application of vibrational energy, induction of absorption atelectasis, or the like. Optionally, diagnostic procedures on the isolated lung segment may be performed, typically using the same isolation/access catheter.

26 Claims, 20 Drawing Sheets

U.S. PATENT DOCUMENTS

| | | |
|---|---|---|
| 3,677,262 A | 7/1972 | Zukowski |
| 3,776,222 A | 12/1973 | Smiddy |
| 3,866,599 A | 2/1975 | Johnson |
| 3,913,568 A | 10/1975 | Carpenter |
| 4,041,936 A | 8/1977 | Carden |
| 4,086,919 A | 5/1978 | Bullard |
| 4,327,720 A | 5/1982 | Bronson et al. |
| 4,327,721 A | 5/1982 | Goldin et al. |
| 4,453,545 A | 6/1984 | Inoue |
| 4,468,216 A | 8/1984 | Muto |
| 4,567,882 A | 2/1986 | Heller |
| 4,716,896 A | 1/1988 | Ackerman |
| 4,742,819 A | 5/1988 | George |
| 4,784,133 A | 11/1988 | Mackin |
| 4,819,664 A | 4/1989 | Nazari |
| 4,846,153 A | 7/1989 | Berci |
| 4,850,371 A | 7/1989 | Broadhurst et al. |
| 4,862,874 A | 9/1989 | Kellner |
| 4,896,941 A | 1/1990 | Hayashi et al. |
| 4,949,716 A | 8/1990 | Chenoweth |
| 4,955,375 A | 9/1990 | Martinez |
| 4,958,932 A | 9/1990 | Kegelman et al. |
| 4,961,738 A | 10/1990 | Mackin |
| 4,976,710 A | 12/1990 | Mackin |
| 5,056,529 A | 10/1991 | de Groot |
| 5,143,062 A | 9/1992 | Peckham |
| 5,146,916 A | 9/1992 | Catalani |
| 5,165,420 A | 11/1992 | Strickland |
| 5,285,778 A | 2/1994 | Mackin |
| 5,309,903 A | 5/1994 | Long |
| 5,331,947 A | 7/1994 | Shturman |
| 5,361,753 A | 11/1994 | Pothmann et al. |
| 5,400,771 A | 3/1995 | Pirak et al. |
| 5,477,851 A | 12/1995 | Callaghan et al. |
| 5,499,625 A | 3/1996 | Frass et al. |
| 5,598,840 A | 2/1997 | Iund et al. |
| 5,642,730 A | 7/1997 | Baran |
| 5,645,519 A | 7/1997 | Lee et al. |
| 5,653,231 A | 8/1997 | Bell |
| 5,660,175 A | 8/1997 | Dayal |
| 5,682,880 A | 11/1997 | Brain |
| 5,707,352 A | 1/1998 | Sekins et al. |
| 5,752,921 A | 5/1998 | Orr |
| 5,893,841 A | 4/1999 | Glickman |
| 5,897,528 A | 4/1999 | Schultz |
| 6,174,323 B1 | 1/2001 | Biggs et al. |
| 6,258,100 B1 | 7/2001 | Alferness et al. |
| 6,287,290 B1 * | 9/2001 | Perkins et al. ............... 604/516 |

OTHER PUBLICATIONS

Criner et al., "Effect of lung volume reduction surgery on diaphram strength" Am. J. Res. Crit. Care Med. (1998) 157:1578–1585.

Harada et al., "Re-expansion of refractory atelectasis using a bronchofiberscope with a balloon cuff" Chest (1983) 84(6):725–728.

Kotloff et al., "Comparison of short-term functional outcomes following unilateral and bilateral lung volume reduction surgery" Chest (1998) 113(4):890–895.

Sclafani, "Clearing the airways" AARC Times (Jan. 1999) pp. 69–71, 97.

* cited by examiner

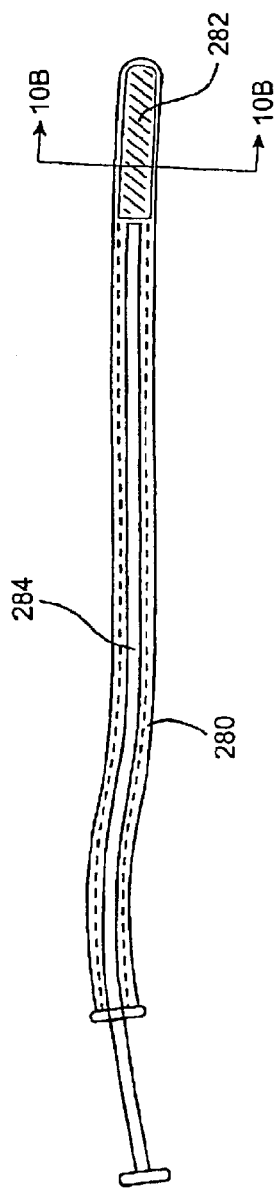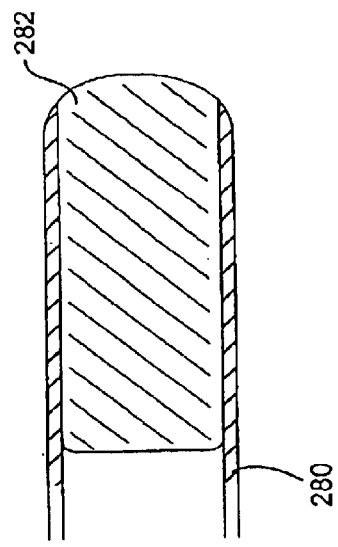

METHODS SYSTEMS AND KITS FOR LUNG VOLUME REDUCTION

CROSS-REFERENCES TO RELATED APPLICATIONS

This application is a continuation-in-part of, and claims the benefit of priority from application Ser. No. 09/347,032, filed on Jul. 2, 1999 now U.S. Pat. No. 6,287,290, the full disclosure of which is incorporated herein by reference.

BACKGROUND OF THE INVENTION

1. Field of the Invention

The present invention relates generally to medical methods, systems, and kits. More particularly, the present invention relates to methods and apparatus for effecting lung volume reduction by aspirating isolated segments of lung tissue.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where the lung is resected, typically using stapling devices having integral cutting blades.

While effective in many cases, conventional lung reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures. For these reasons, it would be desirable to provide improved methods, systems, and kits for performing lung volume reduction which overcome at least some of the shortcomings noted above.

2. Description of the Background Art

WO 99/01076 describes devices and methods for reducing the size of lung tissue by applying heat energy to shrink collagen in the tissue. In one embodiment, air may be removed from a bleb in the lung to reduce its size. Air passages to the bleb may then be sealed, e.g., by heating, to fix the size of the bleb. WO 98/49191 describes a plug-like device for placement in a lung air passage to isolate a region of lung tissue, where air is not removed from the tissue prior to plugging. WO 98/48706 describes the use of surfactants in lung lavage for treating respiratory distress syndrome.

Patents and applications relating to lung access, diagnosis, and treatment include U.S. Pat. Nos. 5,752,921; 5,707,352; 5,682,880; 5,660,175; 5,653,231; 5,645,519; 5,642,730; 5,598,840; 5,499,625; 5,477,851; 5,361,753; 5,331,947; 5,309,903; 5,285,778; 5,146,916; 5,143,062; 5,056,529; 4,976,710; 4,955,375; 4,961,738; 4,958,932; 4,949,716; 4,896,941; 4,862,874; 4,850,371; 4,846,153; 4,819,664; 4,784,133; 4,742,819; 4,716,896; 4,567,882; 4,453,545; 4,468,216; 4,327,721; 4,327,720; 4,041,936; 3,913,568 3,866,599; 3,776,222; 3,677,262; 3,669,098; 3,498,286; 3,322,126; WO 95/33506, and WO 92/10971.

Lung volume reduction surgery is described in many publications, including Becker et al. (1998) Am. J. Respir. Crit. Care Med. 157:1593–1599; Criner et al. (1998) Am. J. Respir. Crit. Care Med. 157:1578–1585; Kotloff et al. (1998) Chest 113:890–895; and Ojo et al. (1997) Chest 112:1494–1500.

The use of mucolytic agents for clearing lung obstructions is described in Sclafani (1999) AARC Times, January, 69–97. Use of a balloon-cuffed bronchofiberscope to reinflate a lung segment suffering from refractory atelectasis is described in Harada et al. (1983) Chest 84:725–728.

SUMMARY OF THE INVENTION

The present invention provides improved methods, systems, and kits for performing lung volume reduction in patients suffering from chronic obstructive pulmonary disease or other conditions where isolation of a lung segment or reduction of lung volume is desired. The methods are minimally invasive with instruments being introduced through the mouth (endotracheally) and/or in some cases through the chest, (e.g., thoracoscopically), and rely on isolating the target lung tissue segment from other regions of the lung. Isolation is usually achieved by introducing an isolation/access catheter endotracheally to the air passages of a lung. By positioning a distal end of an isolation/access catheter within an air passage which opens into a target lung tissue segment, the segment may be isolated by occluding the air passage, typically by inflating an occlusion balloon or other structure on the catheter within the air passage. The target lung tissue segment may then be collapsed by aspirating air (and any other gases or liquids that may have been introduced) from the segment, typically through a lumen in the isolation/access catheter. The aspiration "pressure" should be selected to be in a desired range, therefore neither too high nor too low. Preferred aspiration pressures are in the range from −2 mmHg to −40 mmHg, more preferably between −5 mmHg and −20 mmHg.

Optionally, the air passage may then be sealed, either permanently or with the option to reverse the seal and open up the air passage at a later time. Thus, the seal may be temporary or reversible. Sealing may be accomplished by deploying a plug within the air passage. Suitable plugs include a wide variety of mechanical and biological devices and materials. For example, a variety of mechanical plugs can be formed, e.g., from an expandable frame component and an air impermeable cover. The expandable frame component could be balloon expansible or could be self-expanding. Balloon expansible plugs would typically be delivered by a balloon delivery catheter, while self-expanding plugs would be delivered under radial constraint and deployed by release of such constraint. Other suitable mechanical plugs include one-way valves which would permit gasses to flow outwardly from the isolated lung segment but would prevent or inhibit the inward flow of gasses. Exemplary biological plug materials include swellable collagen matrices which hydrate and expand within the air passage so that they fully occlude the passage.

Other sealing methods include the use of tissue adhesives, such as fibrin glues, cyanoacrylate, etc.; the use of occlusive balloons; the use of self-expanding meshes, coils, and other occlusive structures; the use of energy-induced tissue fusion, such as radiofrequency tissue closure; and the like. Both the mechanical plugs and the biological plugs can be combined with the delivery of a flowable, curable sealant, adhesive, or "glue" to further enhance sealing in two-component systems as described in detail below.

In a first particular aspect of the methods of the present invention, air flow through and from the target lung tissue segment will be enhanced prior to aspiration of the segment. It is an objective of the present invention to aspirate and reduce the volume of the lung tissue segment as completely as possible. In one instance, obstructions to gas flow within the target tissue segment are reduced prior to or during aspiration of the segment. Mucus and other obstructions within the target lung tissue segment (which is diseased and frequently subject to blockages) will interfere with substantially complete aspiration of the segment unless removed, disrupted, or otherwise addressed. In a second instance, where a lack of lung surfactant is a cause of the impeded air flow, the present invention will provide for administering a suitable surfactant prior to or during aspiration of the target lung tissue segment.

In a first specific instance, the present invention reduces gas flow obstructions by inflating the lung tissue segment to a pressure higher than normal respiratory inflation pressures. Optionally, portions or segments of the lung adjacent to the target lung segments may be partially deflated or under-ventilated at the same time that the target segment is being inflated at a higher than normal pressure. For example, airflow into adjacent lung segments can be partially blocked to lower pressure in those segments, causing those segments to partially collapse. In a specific instance, a balloon can be used to partially block the bronchus of the lung with the target lung tissue segment.

Usually, the isolated lung tissue segment will be over inflated to a pressure in the range from 60 cm $H_2O$ to 200 cm $H_2O$, preferably in the range from 100 cm $H_2O$ to 150 cm $H_2O$, usually during the administration of general anesthesia (positive pressure ventilation). If a local anesthesia is being used, the pressure will usually be in the range from 10 cm $H_2O$ to 100 cm $H_2O$, preferably from 30 cm $H_2O$ to 60 cm $H_2O$. The duration of such "over inflation" will typically be in the range from one second to 600 seconds, preferably being in the range from 5 seconds to 60 seconds. Such lung inflation may be repeated more than one time. For example, the lung inflation may be carried out by inflating the isolated lung tissue segment in a pulsatile fashion. Over inflation will usually be performed using the isolation/access catheter which was used to isolate the lung tissue segment. Optionally, it would be possible to inflate regions of the lung percutaneously using a needle introduced through the chest, typically under thoracoscopic observation.

In a second specific instance, gas flow obstructions within the target lung tissue segment may be reduced by introducing an agent which clears the obstructions and/or dilates the air passages to permit gas flow around any blockages. Exemplary agents include mucolytic agents, bronchodilators, surfactants, desiccants, solvents, perfluorocarbons, necrosing agents, absorbents, and the like. Such agents may be introduced through a catheter, typically through the isolation/access catheter which has been used to isolate the target lung tissue segment. Optionally, such agents may be heated, typically to a temperature in the range from 38° C. to 90° C. to enhance activity.

In a third specific instance, gas flow obstructions are reduced by delivering mechanical energy to the lung segment, typically vibratory energy which will break down at least some of the obstructions. Typically, the vibratory energy will be ultrasonic energy, more typically being ultrasonic energy having a frequency in the range from 20 kHz to 20 MHz, usually from 20 kHz to 5 MHz. The mechanical energy will usually be delivered to the target lung tissue segment through a non-compressible fluid introduced to the segment, usually through the isolation/access catheter. It will be appreciated that air is a poor transmission and absorption material for ultrasonic and other vibratory energy. Thus, introducing a noncompressible fluid, such as saline, contrast medium, treatment solution (e.g., mucolytic solution, surfactant solution, etc.), or the like, will enhance transmission and absorption of the energy throughout the target lung tissue segment. The vibratory energy may then be applied either through a catheter which has been introduced endotracheally and then into the target lung tissue segment, or externally using a hand-held or other ultrasonic probe intended to deliver ultrasonic energy transcutaneously. Typically, the vibrational treatment will last for time in the range from 5 seconds to 60 minutes, usually from 30 seconds to 30 minutes.

In a fourth specific instance, the removal of air from diseased portions of the lung prior to sealing of those portions or other procedures may be achieved by ventilation of those diseased portions of the lung with a low molecular weight gas, such as helium or a combination of helium and oxygen A technique to collapse a region of lung is called "absorption atelectasis," where oxygen in the lung is allowed to diffuse into the blood stream. By filling the target region of the lung with pure or highly concentrated oxygen, that region of the lung will collapse as the oxygen is absorbed. Such "pure" oxygen atelectasis may be used in the methods of the present invention. The use of pure or nearly pure oxygen, however, results in carbon dioxide diffusion out of the blood stream and into the target lung segment. Thus, complete collapse of the lung cannot be achieved. The present invention, in contrast, will preferably utilize a low molecular weight gas, such as helium or a combination of helium and oxygen. The air in the target region of the lung will be fully displaced with the low molecular weight gas, and the segment then closed, as described elsewhere herein. The low molecular weight gas or oxygen mixture will readily diffuse into the blood and the segment will collapse with minimum release of carbon dioxide from the blood into the lung. Particularly if a pure low molecular weight gas such as helium is used, there will be very little if any carbon dioxide release back into the lung portion.

In a particularly preferred aspect, the low molecular weight gas or oxygen mixture will be introduced into the lung region in high frequency pulses at relatively low pressures. Exemplary pulse rates are in the range from 1.5 pulses per second to 3 pulses per second, at pressures in the range from 0.25 psi to 2 psi. Such "high frequency ventilation" is particularly effective in displacing air and oxygen initially present in the lung region. Optionally, a catheter used to achieve the high frequency ventilation may include a separate exhaustion port and lumen which may be connected to a separate vacuum source to achieve adequate removal of gasses and replacement with the low molecular weight gas or oxygen mixture.

In a fifth specific instance, the removal of air from a diseased region of the lung may be enhanced by perfusion or infusion with a perfluorocarbon liquid. One problem with removal of gasses from a diseased region of the lung is that the lung passages therein may be blocked with mucous and other secretions. Ventilating the lung with a perfluorocarbon liquid can displace such secretions, causing them to rise to the top or meniscus of the liquid in the lung. Preferably, the entire lung may be treated with the perfluorocarbon liquid, where the patients are being mechanically ventilated. Alternatively, such treatment could be specifically directed at the diseased region of the lung immediately prior to the lung resection techniques described elsewhere herein. The techniques may be performed while the lung portion is isolated, typically using an isolation catheter having an inflatable cuff as described elsewhere herein. The perfluorocarbon liquid may be introduced through the catheter while the patient is positioned so that the liquid meniscus preferably lies near the catheter when the lung portion is filled. Perfluorocarbon liquid may then be removed after the mucus and other secretions have been dislodged and floated to the meniscus. The lung may then be aspirated and collapsed for treatment according to the other aspects of the present invention.

In a second aspect of the methods of the present invention, collapse of the target isolated lung tissue segment is enhanced by applying external pressure to the isolated segment. The external pressure will usually be applied through the chest, e.g., thoracoscopically. Most simply, a safety needle can be introduced to a pleural space over the lung, typically intracostally (between adjacent ribs). The pleural space can then be insufflated, e.g., carbon dioxide or other gas inflation medium introduced to the pleural space, in order to increase pressure on the lung and enhance collapse of the target segment. Simultaneously, the target segment will be aspirated so that the combined lowering of the internal pressure and raising of the external pressure work to substantially completely collapse the segment. Alternatively, the external pressure may be applied by inflating a balloon in the pleural space over the target lung tissue segment. Still further optionally, the external pressure may be applied by a probe which is engaged and pushed against at least a portion of the external surface of the lung overlying the target segment. Optionally, a thoracoscopically or other percutaneously placed needle could be used to puncture and aspirate a portion of the lung, typically in conjunction with a catheter-based aspiration as described elsewhere herein. For example, portions of the lung which could not be collapsed using an internal catheter could be targeted with an external needle by thoracoscopic visualization. Any puncture holes left in the lung could then be sealed with a suitable adhesive, such as a fibrin glue.

In a third aspect of the present invention, methods for reducing lung volume by isolating the lung tissue segment and aspirating the isolated segment are combined with diagnostic methods which permit, for example, determination of whether the segment which has been accessed and isolated is in fact diseased and should be collapsed. The diagnostic methods and steps may take a wide variety of forms. For example, the isolation/access catheter or other endotracheally introduced catheter may be used to measure air flow to and from the lung tissue segment to determine whether the air flow capabilities of that segment are impaired. Alternatively or additionally, the isolation/access catheter may be used to measure carbon dioxide concentrations within the target lung tissue segment. Other parameters which may be measured include forced expiratory volume, pressure, pressure/volume P/V curves, segment compliance curves, work of breathing data, perfusion scans, bronchograms, or the like.

In a still further aspect of the methods of the present invention, a target lung tissue segment is isolated and aspirated, where the segment is collapsed to a volume which is no greater than 40% of its inflated size prior to aspiration, usually being no greater than 30%, and preferably being no greater than 20%. The inflated size is its maximum size at peak inspiratory pressure, assumed to be 40 cm $H_2O$ for patients undergoing positive pressure ventilation, the spontaneous respiratory pressure is assumed to be 90 cm $H_2O$. The change in volume may be determined by conventional techniques, such as thoracoscopy (X-ray), CT scans, MRI, ultrasound imaging, bronchograms, PFT (pulmonary function testing), gas dilution techniques, and the like.

Such efficient collapsing of the target lung tissue segment may be achieved in any of the ways discussed above. Additionally, it may be achieved by inducing absorption atelectasis prior to aspiration. Most simply, absorption atelectasis can be induced by insufflating the isolated lung tissue segment with high oxygen concentrations prior to aspiration. The oxygen concentrations in the insufflation gas should be at least 50% by volume, preferably 75% by volume, and more preferably being substantially pure oxygen. Alternatively, collapsing of the lung may be facilitated by infusion or lavage of the lung with a low molecular weight gas or oxygen and low molecular weight gas combination, as generally described above.

The present invention further provides systems for performing intraluminal lung volume reduction procedures according to the methods of the present invention. The systems comprise at least an isolation or access catheter having a proximal end, a distal end, an occlusion element near the distal end, and at least one lumen therethrough. The isolation/access catheters are used for establishing access and isolation of a target lung tissue segment, typically by endotracheal introduction into the air passages of the lung. In a first system according to the present invention, the isolation/access catheter is combined with a sealing catheter which carries a closure element. A sealing catheter is adapted to be introduced through the lumen of the isolation/access catheter, and the closure element is adapted to be deployed from the isolation/access catheter within an air passage leading to the target tissue segment. The closure element typically comprises a swellable plug, such as a partially hydrated collagen plug. Deployment within the air passage thus permits the plug to swell in situ and completely block the air passage leading into the target tissue segment so that, once the segment is collapsed, air will not enter to reinflate the segment. Surprisingly, it has been found that such occlusion will substantially inhibit reinflation of the lung, and that there is little significant collateral air flow into the collapsed region.

In a second system, according to the present invention, the isolation/access catheter is combined with a reagent capable of either clearing dilating, or widening the air passages in order to facilitate substantially complete aspiration of the target tissue segments. Exemplary reagents have been set forth above.

In a third system, the isolation/access catheter is combined with probes intended for percutaneous introduction to apply external pressure over the lung. The probes may be in the form of a needle, a balloon, or a simple engagement element intended for pressing inwardly against the lung.

The present invention still further comprises kits which include at least an isolation/access catheter as described above. The kits will further comprise instructions for use according to any of the methods set forth above. For example, the instructions for use may set forth that the isolated lung tissue segment is to be over inflated in order to reduce blockages therein. Alternatively, the instructions for use may set forth that certain agents (as described above) are to be introduced to the segment in order to breakdown obstructive materials prior to aspiration. Still further, the kit instructions may set forth that the lung is to be externally collapsed by applying pressure or other external force to a target tissue segment prior to or simultaneous with aspiration of that segment. Still further, the instructions may set forth that the volume of the target lung tissue segment is to be reduced by at least the percentages set forth above. In all cases, the kits will usually further comprise packaging, such as a pouch, tray, tube, box, or the like for holding the kit components together with the instructions for use. The instructions for use may be printed on a separate sheet (commonly referred to as a package insert) and/or may be printed on the packaging itself. Usually, the kit components which will be introduced to the patient will be sterilized and packaged in a sterile manner within the kit.

BRIEF DESCRIPTION OF THE DRAWINGS

FIGS. 10A–10C illustrate a sealing catheter carrying a swellable closure element which may be used in the methods, systems, and kits of the present invention.

DESCRIPTION OF THE SPECIFIC EMBODIMENTS

Lung volume reduction is performed by collapsing a target lung tissue segment, usually within sub-lobular regions of the lung which receive air through a single air passage, i.e., segment of the branching bronchus which deliver to and receive air from the alveolar regions of the lung. Such isolated lung tissue segments are first isolated and then collapsed by aspiration of the air (or other gases or liquids which may have been introduced, as discussed below) from the target lung tissue segment. Lung tissue has a very high percentage of void volume, so removal of internal gases can reduce the lung tissue to a small percentage of the volume which it has when fully inflated, i.e. inflated at normal inspiratory pressures. The exemplary and preferred percentages for the volume reduction are set forth above.

In particular, the present invention provides methods and apparatus for enhancing the aspiration and collapse of the target lung tissue segment. Such methods and apparatus may involve one or more of the following improvements. First, various approaches may be taken to remove or lessen obstructions to gas flow within the target tissue region. Second, methods and apparatus may be employed to apply external pressure over the lung to enhance the collapse achieved by internal aspiration. Third, aspiration of the gases within the target tissue segment may be enhanced by inducing absorption atelectasis prior to aspiration. Absorption atelectasis may be induced, for example, by introducing an oxygen-rich gas to the lung tissue segment, usually at least 50% oxygen by volume, more usually at least 75% oxygen by volume, and preferably substantially pure oxygen. Absorption atelectasis is a phenomena which occurs when an enriched oxygen mixture is inspired. The high oxygen concentration causes an increase in the partial oxygen pressure which in turn causes the rate of oxygen transfer into the capillary blood within the alveolar regions to increase greatly. The increased oxygen flux may increase so much that the net flow of gas into the blood exceeds the inspired flow of gas, causing the lung unit to become progressively smaller. Fourth, the access methods and apparatus may be used for performing in situ diagnosis, usually as part of the collapse procedure. Any one of a number of lung performance characteristics may be measured, typically by sampling using the isolation/access catheter.

Figure 1:
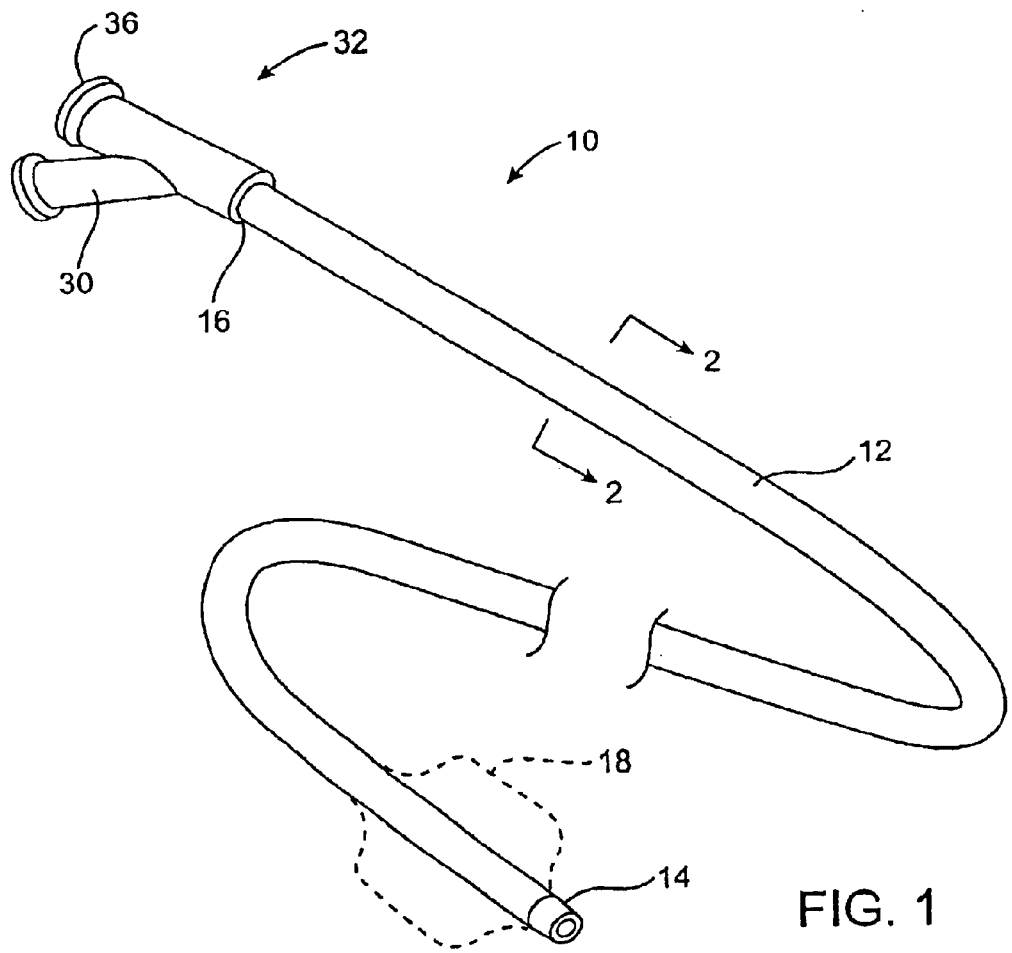
FIG. 1 is a perspective illustration of an isolation/access catheter useful in the methods, systems, and kits of the present invention.
Figure 2:
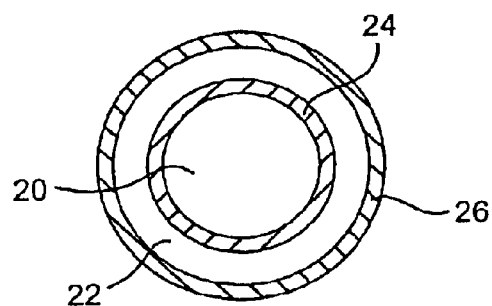
FIG. 2 is a cross-sectional view taken along line 2 to a FIG. 1.

The methods of the present invention will generally rely on accessing the target lung tissue segment using an isolation/access catheter adapted to be introduced endotracheally into the bronchus of the lung. An exemplary isolation/access catheter 10 is illustrated in FIGS. 1 and 2 and comprises a catheter body 12 having a distal end 14, a proximal end 16, an inflatable occlusion balloon 18 near its distal end, and at least one lumen therethrough. Usually, the catheter will have at least two lumens, and catheter 10 includes both a central lumen 20 and an annular lumen 22 defined by inner body member 24 and outer body member 26 which is coaxially disposed about the inner body member. The annular lumen 22 opens to port 30 on a proximal hub 32 and provides for inflation of balloon 18. The central lumen 20 opens to port 36 on hub 32 and provides for multiple functions, including optional introduction over a guidewire, aspiration, introduction of secondary catheters, such as sealing catheters described below, and the like.

Figure 4A:
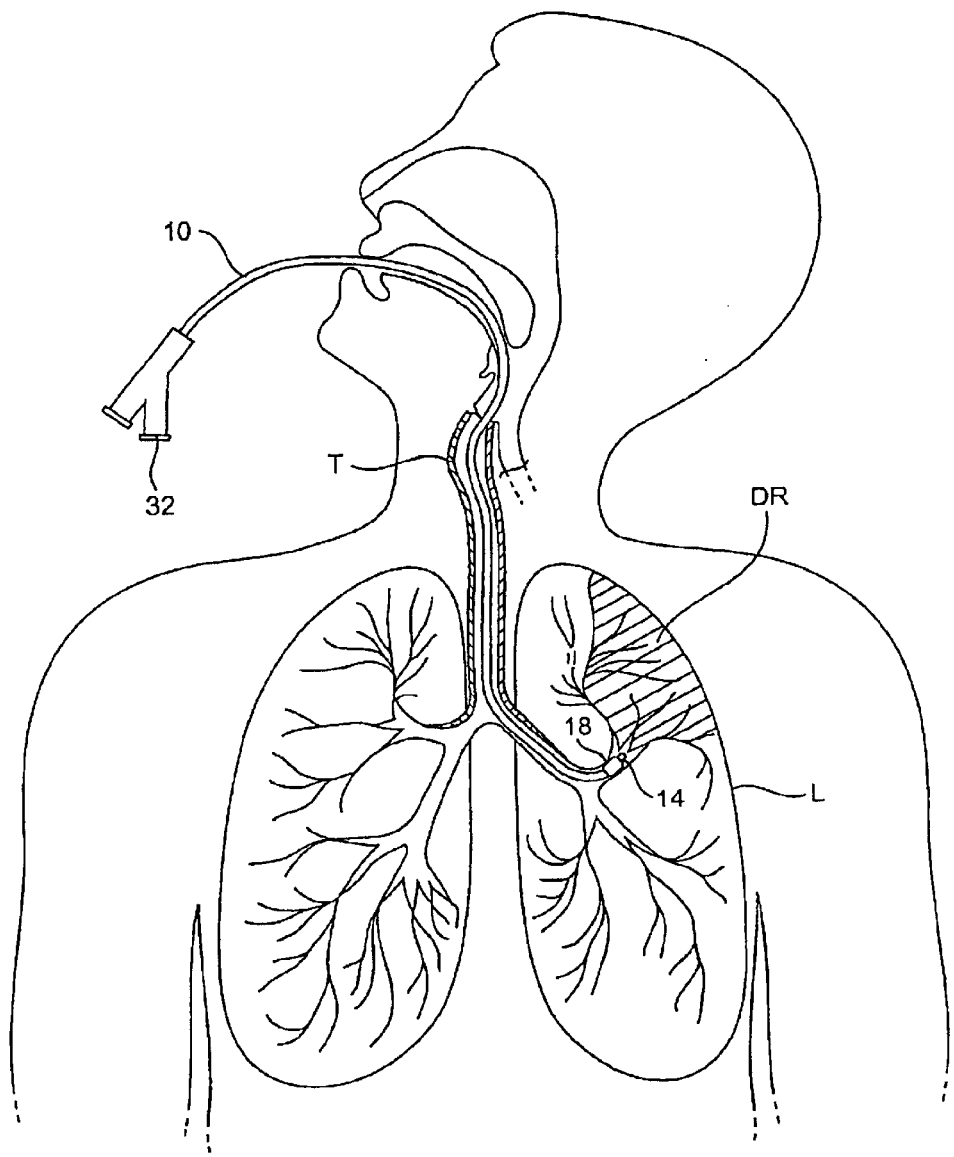
FIGS. 4A–4C illustrate use of the isolation/access catheter of FIG. 1 for isolating and collapsing a target lung tissue segment according the to the methods of the present invention.
Figure 4B:
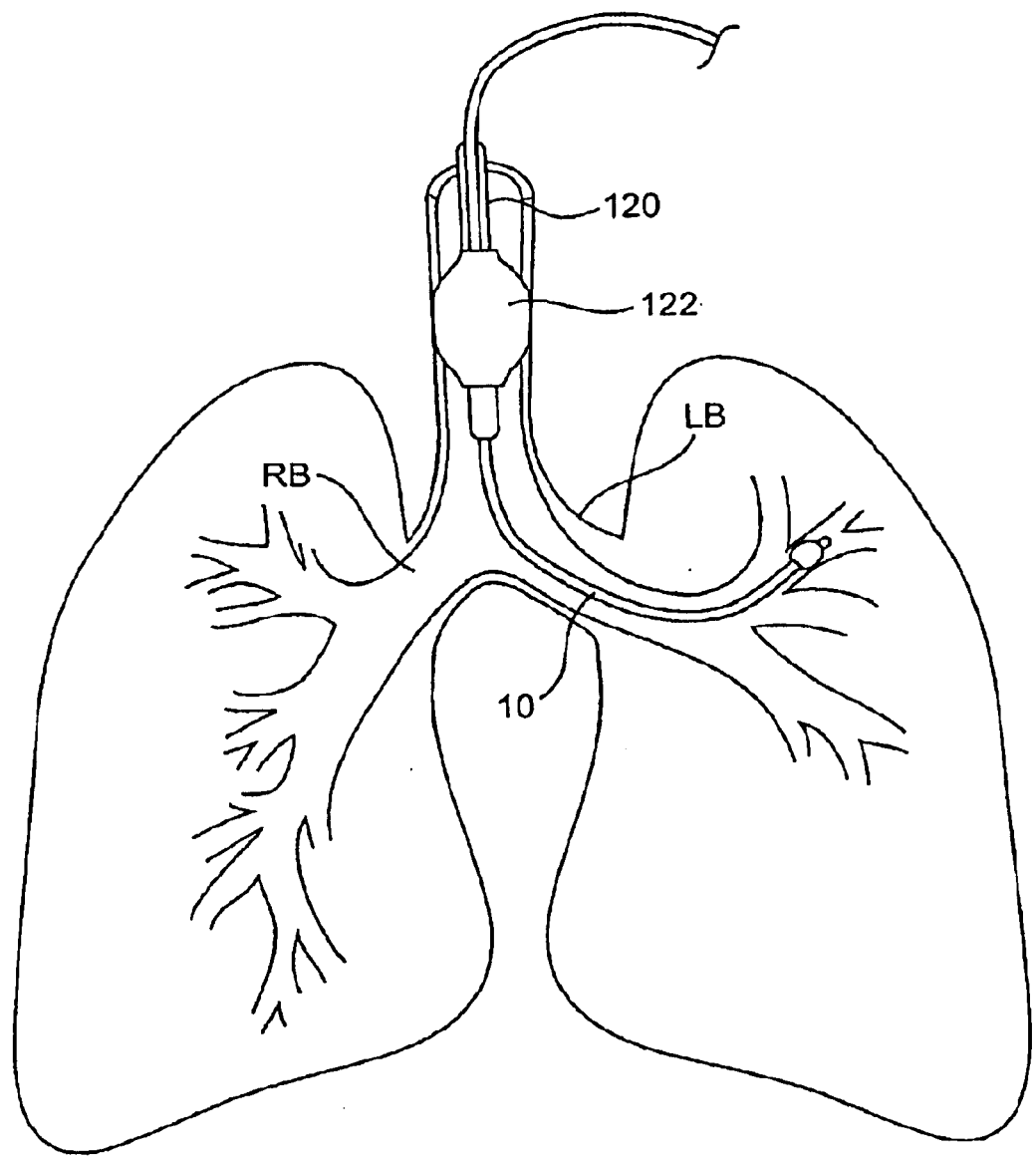

The dimensions and materials of isolation/access catheter 10 are selected to permit endotracheal introduction and intraluminal advancement through the lung bronchus, optionally over a guidewire and/or through a primary tracheal tube structure (as illustrated in FIG. 4B below). Suitable materials include low and high density polyethylenes, polyamides, nylons, PTFE, PEEK, and the like, particularly for the inner tubular member 24. The outer member, including the occlusion balloon, can be made from elastomeric materials, such as polyurethane, low density polyethylene, polyvinylchloride, silicone rubber, latex, and the like. Optionally, portions of the outer tubular member 26 proximal to the inflatable balloon can be made thicker and/or reinforced so that they do not dilate upon pressurization of the balloon. Exemplary dimensions for the isolation/access catheter 10 are set forth in the table below.

| ISOLATION/ACCESS CATHETER DIMENSIONS | | | | |
|---|---|---|---|---|
| | Exemplary | | Preferred | |
| | Inner Tubular Member | Outer Tubular Member | Inner Tubular Member | Outer Tubular Member |
| Outer Diameter (mm) | 0.4–4 | 0.6–4.5 | 1–1.5 | 2–4 |
| Wall Thickness (mm) | 0.05–0.25 | 0.5–0.25 | 0.1–0.2 | 0.15–0.25 |
| Length (cm) | 50–150 | same | 50–80 | same |
| Balloon Length (mm) | 5–50 | | 10–20 | |
| Balloon Diameter (mm) (inflated) | 2–20 | | 6–15 | |

Figure 3A:
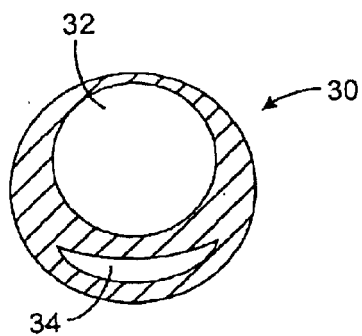
FIGS. 3A–3F illustrate alternative cross-sectional views of the isolation/access catheter of FIG. 1.
Figure 3B:
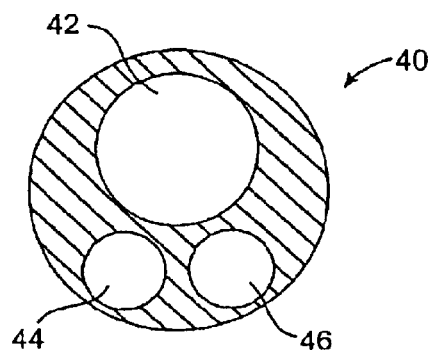
Figure 3C:
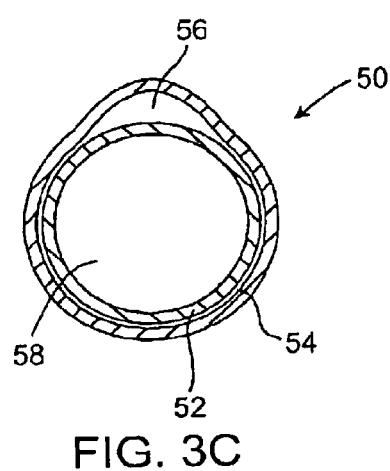
Figure 3D:
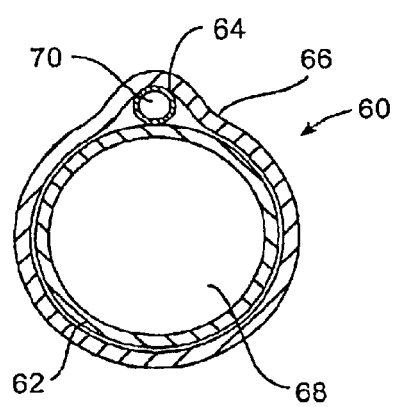

The isolation/access catheter 10 may be modified in a number of ways, some of which are illustrated in FIGS. 3A–3F. For example, instead of an inner and outer coaxial tube construction, the catheter can be a single extrusion having a catheter body 30 with a circular main lumen 32 and a crescent-shaped inflation lumen 34, as illustrated in FIG. 3A. Alternatively, catheter body 40 may be formed as a single extrusion having three lumens, i.e., a primary lumen 42 for receiving a guidewire, applying aspiration, and/or delivering secondary catheters. A second lumen 44 can be provided for inflating the occlusion balloon, and a third lumen 46 can be provided as an alternative guidewire or aspiration lumen. Catheter body 50 comprising a main tubular body 52 having an outer layer 54 fused thereover to define a lumen 56 suitable for balloon inflation as shown in FIG. 3C. A primary lumen 58 is formed within the main tubular member 52. As a slight alternative, catheter body 60 can be formed from a primary tubular member 62, and a secondary tubular member 64, where the tubular members are held together by an outer member 66, such as a layer which is applied by heat shrinking. The primary tubular member 62 provides the main lumen 68 while secondary tube 64 provides a secondary lumen 70. The secondary lumen 70 will typically be used for balloon inflation, while the primary lumen 68 can be used for all other functions of the isolation/access catheter.

Figure 3E:
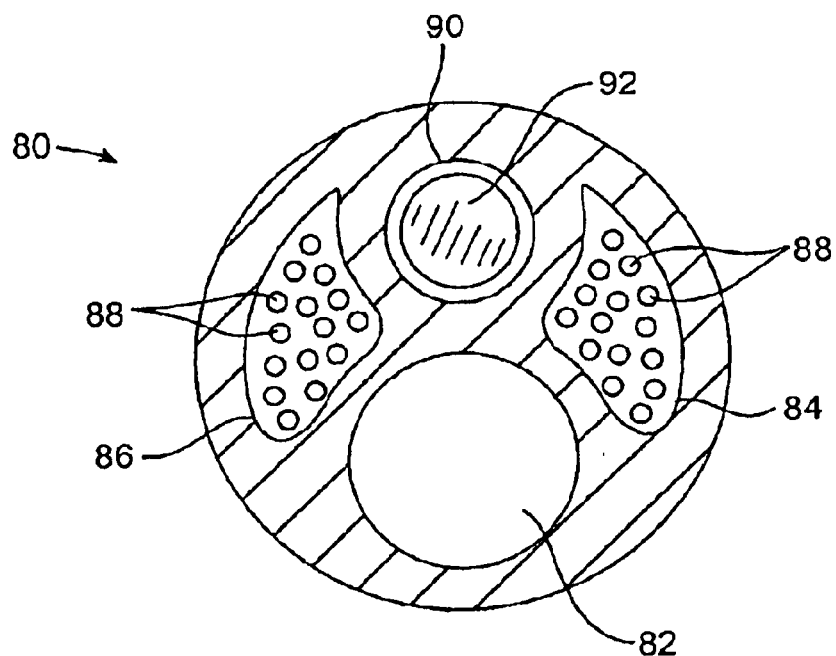
Figure 3F:
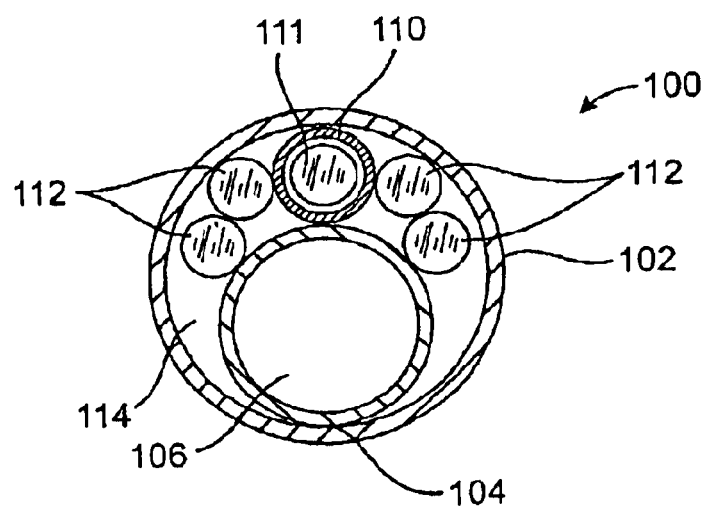

Optionally, the isolation/access catheter in the present invention can be provided with optical imaging capability. As shown in FIG. 3E, catheter body 80 can be formed to include four lumens, typically by conventional extrusion processes. Lumen 82 is suitable for passage over a guidewire. Lumens 84 and 86 both contain light fibers 88 for illumination. Lumen 90 carries an optical wave guide or image fiber 92. Lumen 82 can be used for irrigation and aspiration, typically after the guidewire is withdrawn. Balloon inflation can be effected through the space remaining and lumens 84 and 86 surrounding the light fibers 88. A second catheter body 100 is formed as a coaxial arrangement of a number separate tubes. Outer tube 102 contains a separate guidewire tube 104 defining lumen 106 which permits introduction over a guidewire as well as perfusion and aspiration after the guidewire is removed. Second inner tubular member 110 will carry an optical image fiber 112 and a plurality of light fibers 112 are passed within the remaining space 114 within the outer tubular member. In both catheter constructions 80 and 100, forward imaging can be effected by illuminating through the light fibers and detecting an image through a lens at the distal end of the catheter. The image can be displayed on conventional cathode-ray or other types of imaging screens. In particular, as described below, forward imaging permits a user to selectively place the guidewire for advancing the catheters through a desired route through the branching bronchus.

Referring now to FIG. 4A, a catheter 10 can be advanced to a diseased region DR within a lung L through a patient's trachea T. Advancement through the trachea T is relatively simple and will optionally employ a guidewire to select the advancement route through the branching bronchus. As described above, steering can be effected under real time imaging using the imaging isolation/access catheters illustrated in FIGS. 3E and 3F. Optionally, the isolation/access catheter 10 may be introduced through a visualizing tracheal tube, such as that described in U.S. Pat. No. 5,285,778, licensed to the assignee of the present application. The visualizing endotracheal tube 120 includes an occlusion cuff 122 which may be inflated within the trachea just above the branch of the left bronchus and right bronchus LB and RB, respectively. The visualizing endotracheal tube 120 includes a forward-viewing optical system, typically including both illumination fibers and an image fiber to permit direct viewing of the main branch between the left bronchus LB and right bronchus RB. Thus, initial placement of isolation/access catheter can be made under visualization of the visualizing endotracheal tube 120 and optionally the isolation/access catheter 10 itself. Referring again in particular to FIG. 4A, the isolation/access catheter 10 is advanced until its distal end 14 reaches a region in the bronchus which leads directly into the diseased region DR. Once in place, the balloon 18 can be inflated and the lung tissue segment which includes the diseased region isolated from the remainder of the lung. By isolated, it is meant that air or other gases will not pass between the isolated region and the remaining portions of the lung to any significant extent.

Figure 4C:
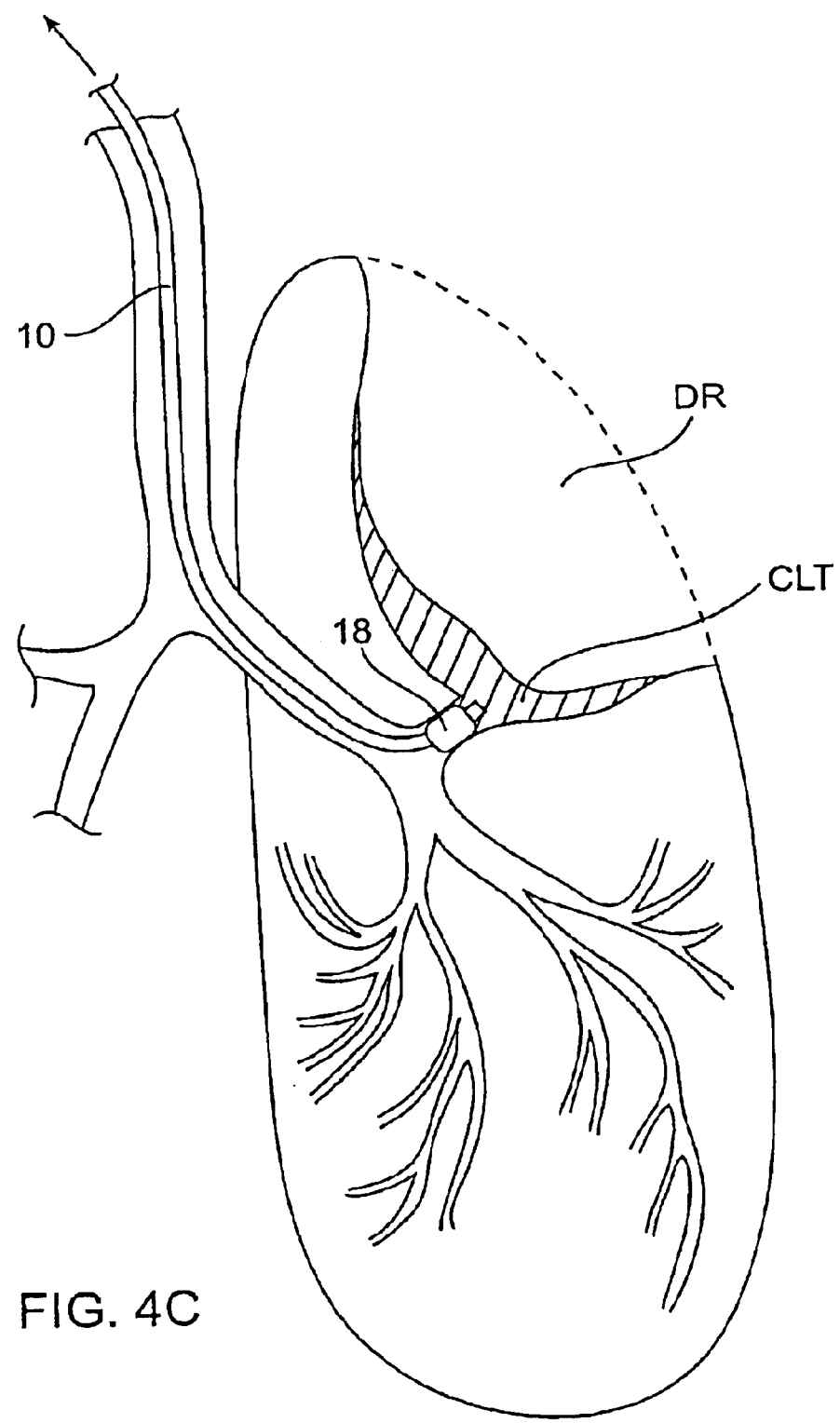

As shown in FIG. 4C, it is the object of the present invention to apply a vacuum to a lumen within the isolation/access catheter 10 to aspirate the internal regions within the isolated lung tissue segment in order to collapse the tissue. This results in a collapsed lung tissue region CLT, as shown as a shaded region in FIG. 4C.

According to the present invention, a variety of steps and protocols may be performed prior to aspirating the isolated lung tissue region in order to enhance gas removal from the region. The region may be over inflated, subjected to vibrations, subjected to a dilating or mucolytic agent, or otherwise treated in order to remove gas flow obstructions within the region. Each of these methods has been well described above and will generally rely on performance of at least one aspect of the procedure using a lumen of the isolation/access catheter 10. For example, over inflation can be effected simply by introducing an inflation gas through the isolation/access catheter to a desired pressure. Pressure may be measured using a transducer at the distal tip of the catheter 10, but will usually be measured statically at a location proximal of the catheter. Alternatively or additionally, an oxygen-rich gas can be introduced through the isolation/access catheter in order to induce absorption atelectasis. For vibratory stimulation incompressible fluid may be introduced through the isolation/access catheter. Stimulation may be imparted using an external probe and/or a vibratory catheter which is introduced through an access lumen of the isolation/access catheter.

Figure 4D:
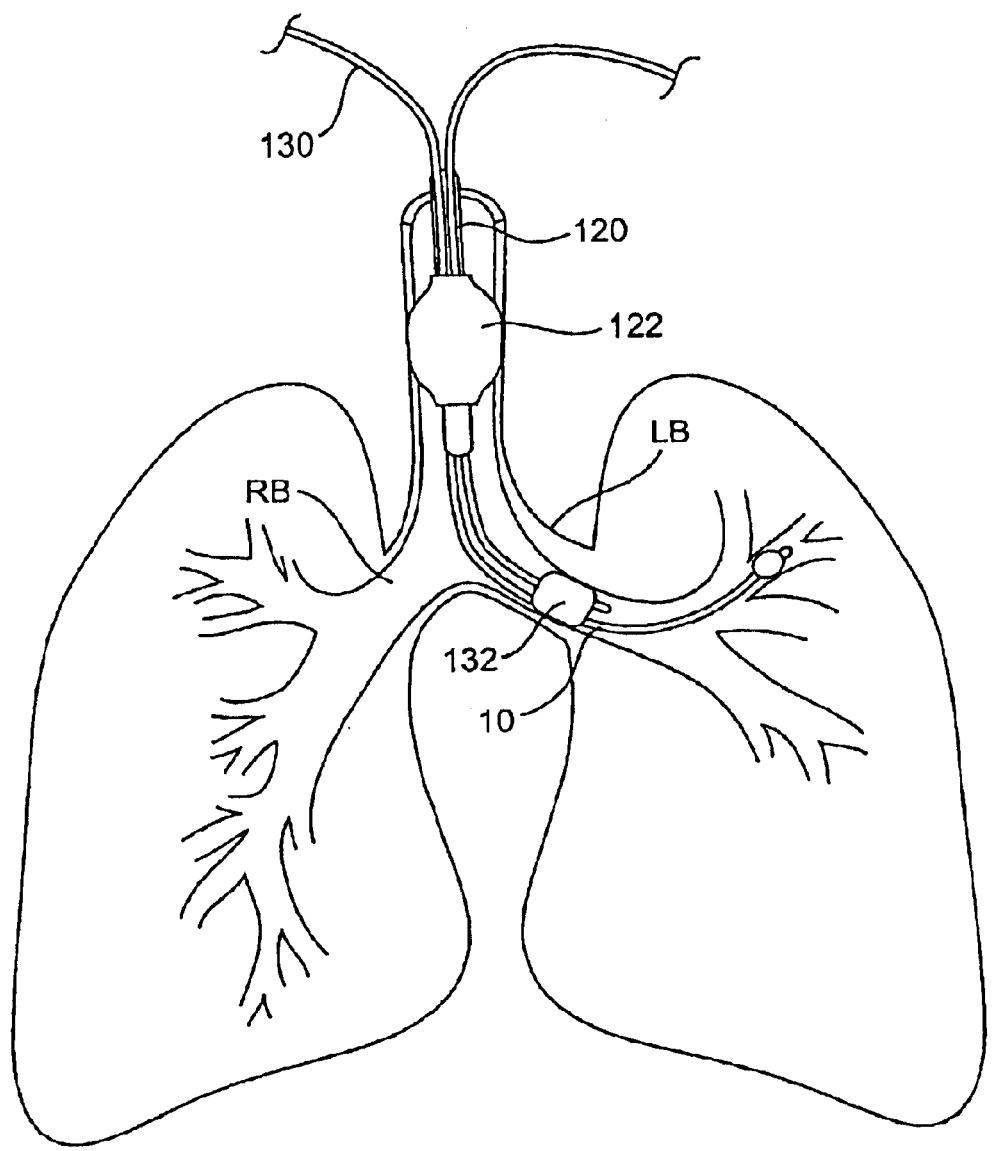
FIG. 4D illustrates one protocol for over inflating a target lung tissue segment prior to aspiration according to the present invention.

As shown in FIG. 4D, in some instances it will be desirable to reduce or selectively control the inflation of the lung tissue adjacent to the target lung tissue segment in order to enhance aspiration of the target segment. For example, an entire one-half lung can be selectively controlled by an isolation or shunting catheter having a balloon 132 near its distal end. The balloon is inflated to occlude a portion of the selected bronchus, typically about 60% of the area. Thus, pressure within the lung can be reduced and the lung partly collapsed other than in the isolated region. In this way, inflation of the target lung tissue segment can be enhanced which can assist in breaking up occlusions within the lung which would otherwise interfere with subsequent aspiration of the segment.

Figure 5:
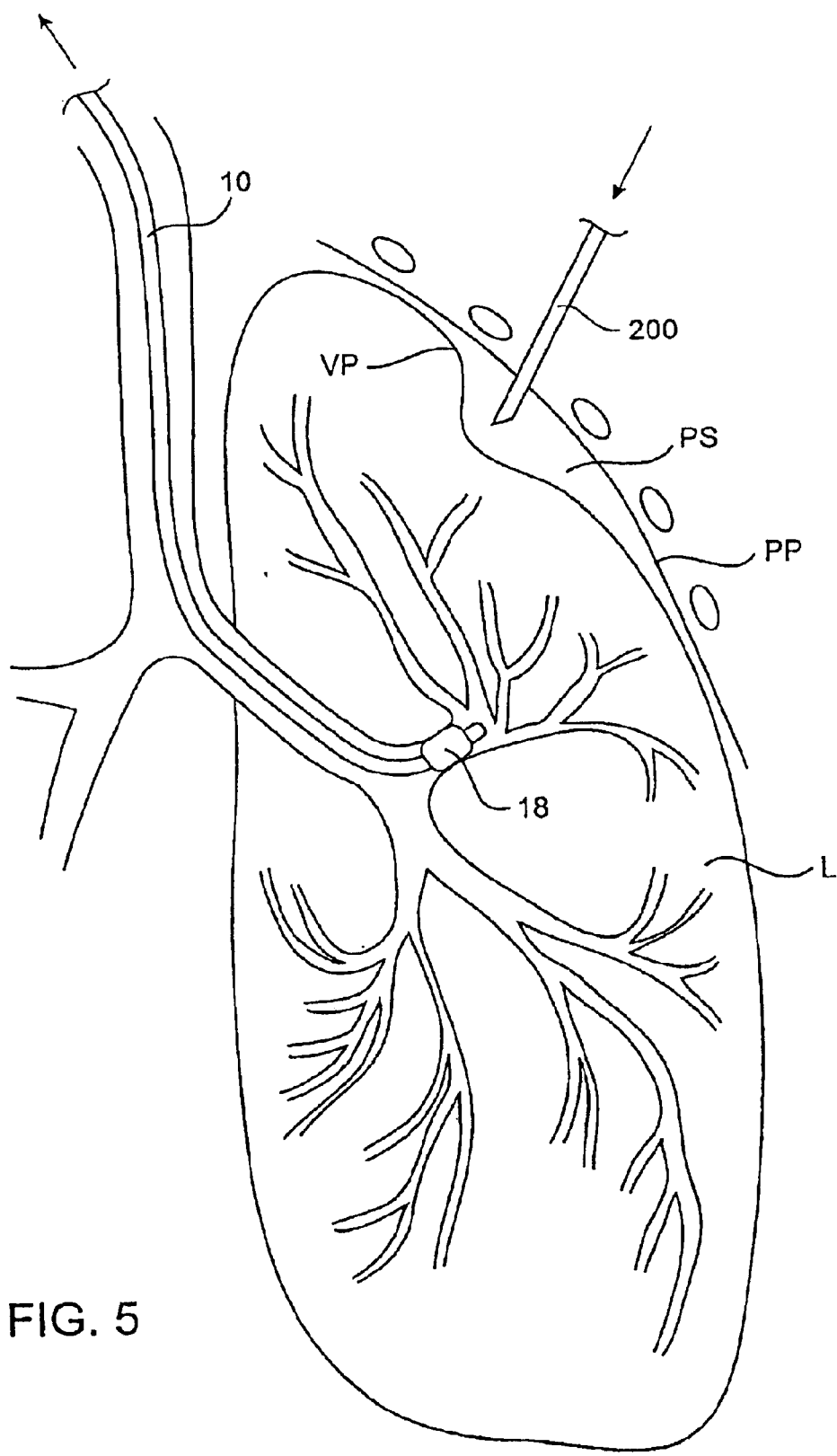
FIG. 5 illustrates an optional aspect of the present invention where an insufflation gas is introduced to aid in the collapse of the target segment from the pleural space.
Figure 6:
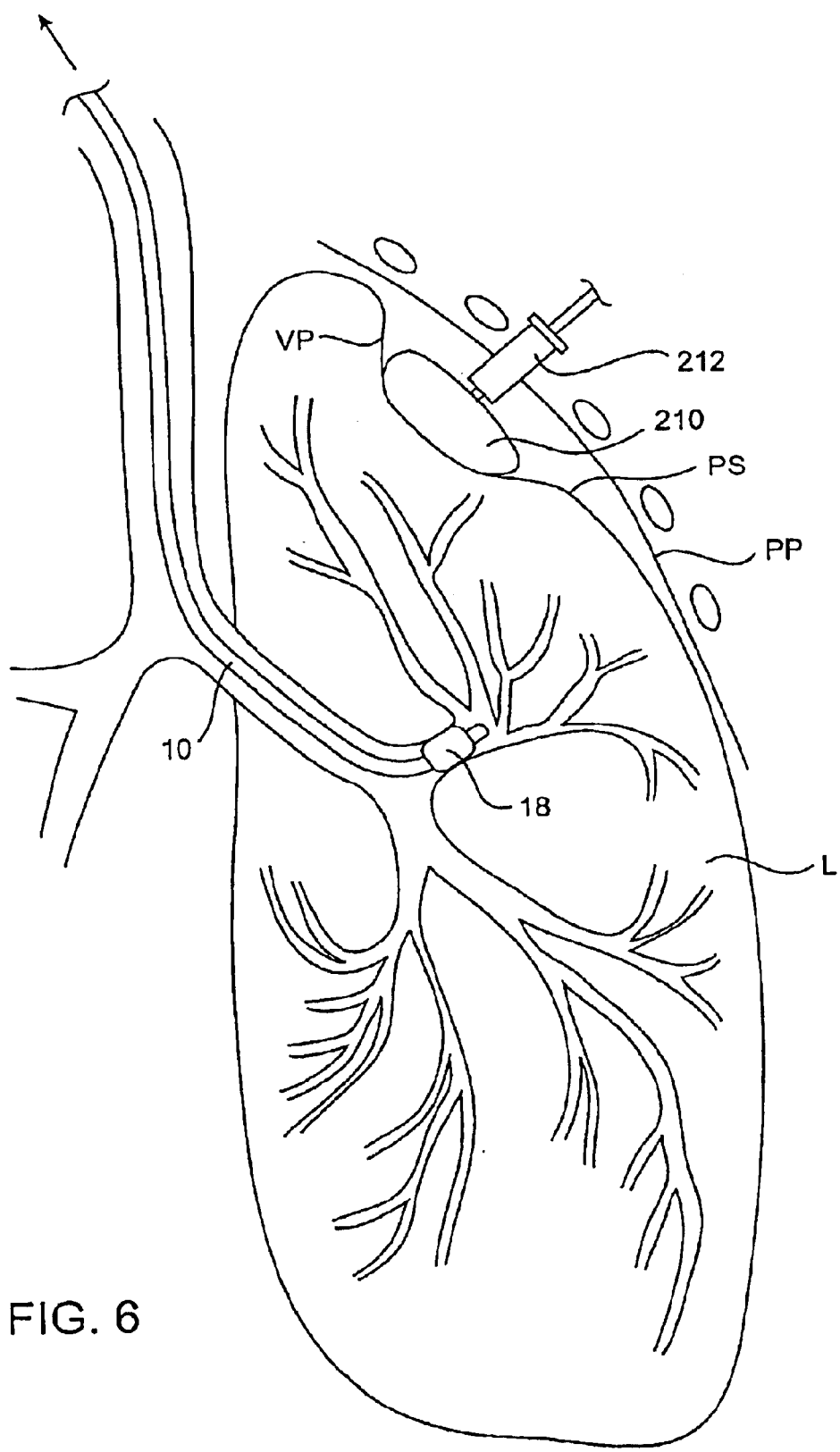
FIG. 6 illustrates an alternative optional aspect of the present invention where an inflatable balloon is used to externally collapse a portion of a target lung tissue segment.

In addition to such in situ techniques for enhancing lung aspiration and collapse, the present invention can rely on application of an external force to assist in collapse. As illustrated in FIG. 5, a needle or other cannula 200 can be percutaneously introduced into a peritoneal space PS between the parietal pleural PP and visceral pleural VP. Insufflation gas, such as carbon dioxide, can be introduced through the needle 200, either using a syringe or other pressure source. The gas will typically be introduced to a pressure in the range from 30 cm $H_2O$ to 200 cm $H_2O$ in spontaneously breathing patients and 70 cm $H_2O$ to 250 cm $H_2O$ in positive pressure ventilated patients.

Figure 7A:
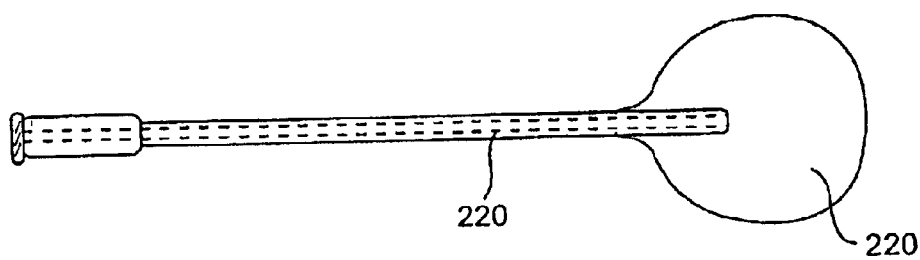
FIGS. 7A–7D illustrate alternative balloon designs for use in external collapse of the target lung tissue segment.
Figure 7B:
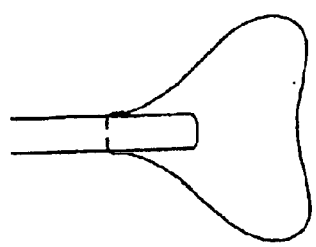
Figure 7C:
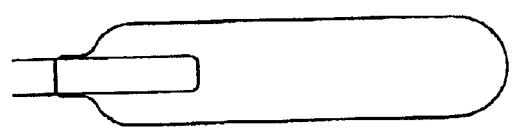
Figure 7D:
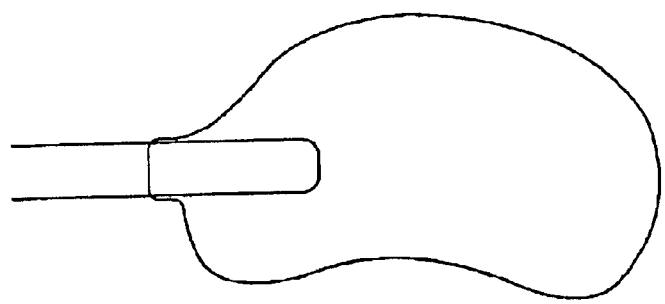

Use of an unconstrained insufflation gas, however, is disadvantageous since it is not directed at a particular target location. In order to more specifically direct an external pressure against the lung, a balloon 210 can be introduced to the pleural space, typically through a thoracic trocar 212. The balloon can be placed based on fluoroscopic observation. Depending on the particular area which is to be collapsed, a variety of specific balloon configurations can be employed, as illustrated in FIGS. 7A–7D. A generally spherical balloon 220 is shown attached to shaft 220 in FIG. 7A. Other configurations include a winged profile (FIG. 7B), a cylindrical or spatula profile (FIG. 7C), and a convex profile (FIG. 7D). Each of these will be attached to a shaft which permits inflation after introduction into the pleural space.

Figure 8:
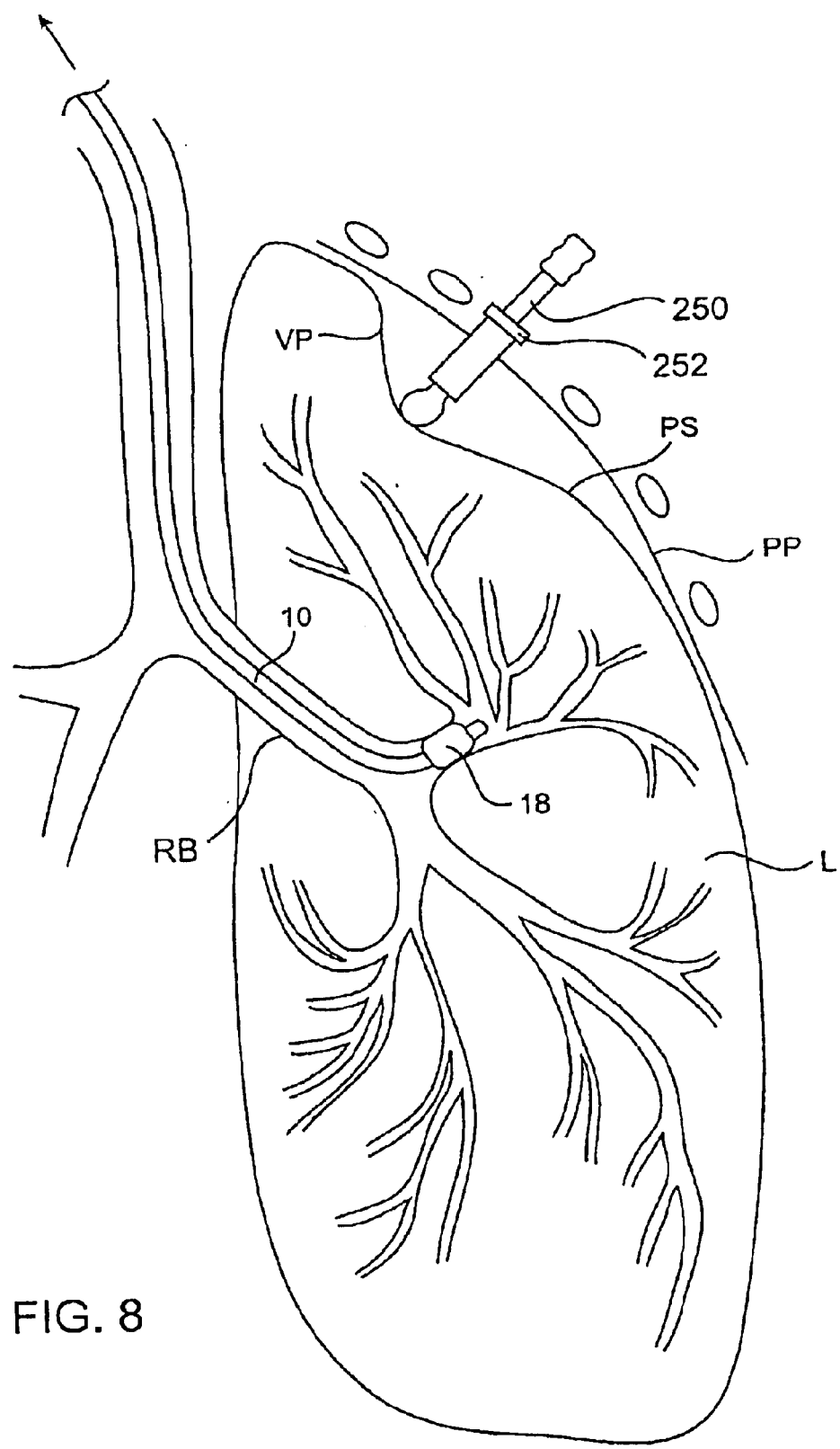
FIG. 8 illustrates yet another alternative optional aspect of the methods of the present invention where a probe is used to engage and collapse a portion of a target lung tissue segment.
Figure 9A:
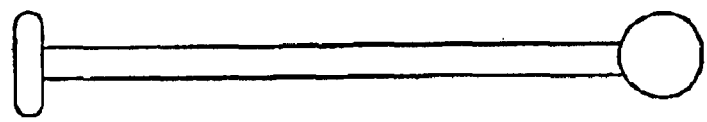
FIGS. 9A–9C illustrate alternative probe designs.
Figure 9B:
Figure 9C:
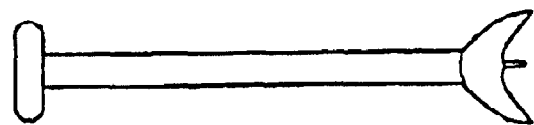

As a further alternative to needle insufflation and balloon expansion, a target lung tissue segment can be externally collapsed using a simple probe 250, usually introduced through a thoracic trocar 252, as shown in FIG. 8. A variety of probes for mechanically engaging and compressing the outer lung surface are illustrated in FIGS. 9A–9C. Optionally, a needle can be used to puncture at a desired point in the target tissue lung segment in order to release and/or aspirate air, usually as a supplement to a primary catheter-based aspiration. The puncture can then be sealed with fibrin glue or other suitable sealant.

Figure 11:
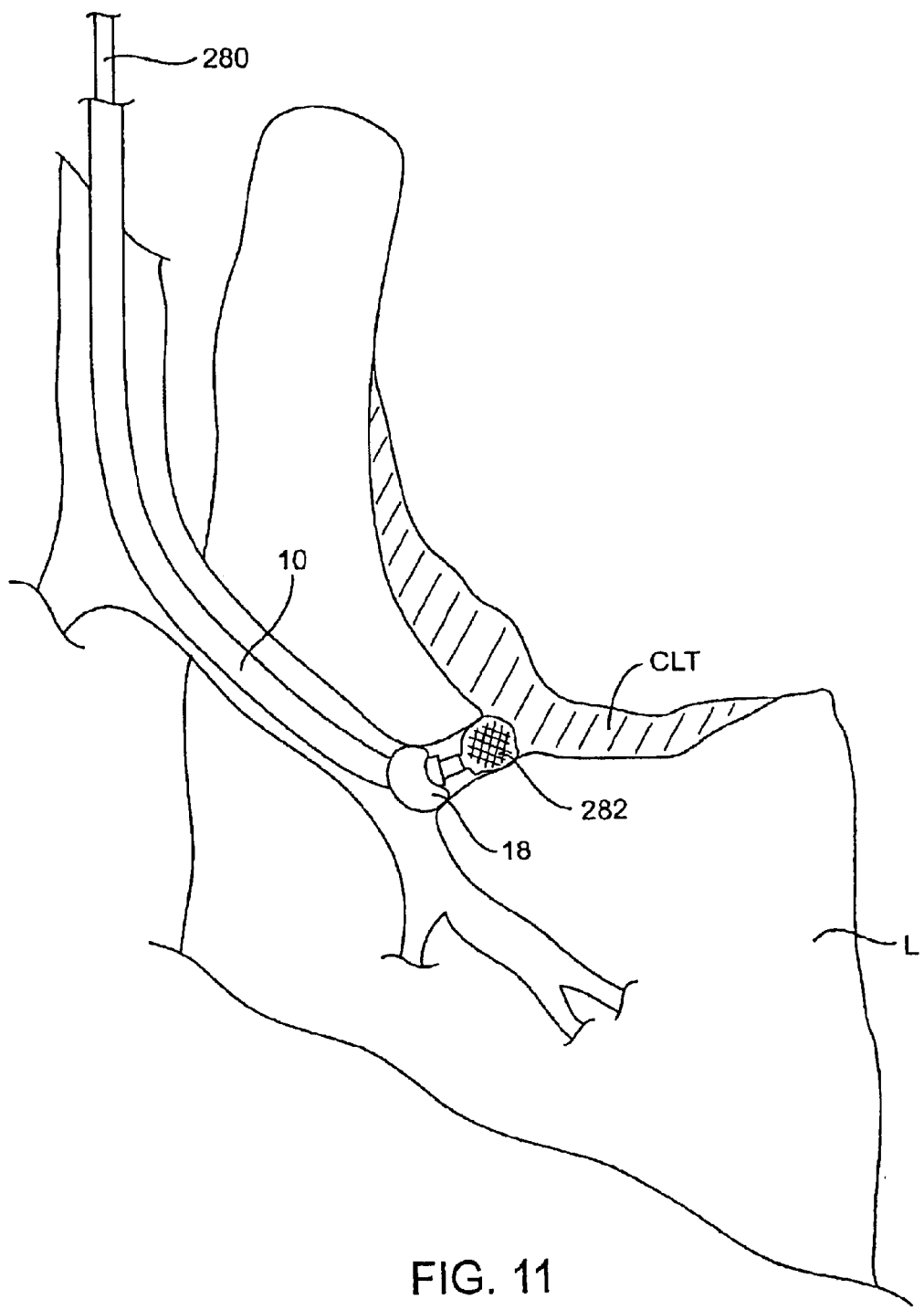
FIG. 11 illustrates use of the sealing catheter of FIGS. 10A–10C for selectively occluding an air passage leading to a target lung tissue segment according to the methods of the present invention.

The methods of the present invention will optionally comprise sealing or occluding the air passage leading to the collapsed tissue region CLT. Such sealing can be performed in a variety of ways, including suturing, gluing, energy-mediated tissue adhesion, and the like. In a preferred aspect of the present invention, a sealing catheter 280 can be used to deliver a plug 282, typically a partially hydrated collagen hydrogel as illustrated in FIGS. 10A–10C. Usually, the catheter wilt have dimensions which permit it to be introduced through the main access lumen of isolation/access catheter 10. The plug 282 will be contained in the distal tip of a lumen in the catheter, and a push rod 284 extends the length of the catheter to permit the treating physician to deploy the plug 282 after the tip of the catheter is properly located, as illustrated in FIG. 11, usually while the balloon on the isolation/access catheter remains inflated and the target lung tissue remains sealed and in an aspirated, collapsed configuration. Once deployed within the moist environment of the lung bronchus, the plug 282 will absorb water and will swell substantially, typically from 100% to 1000% in order to fully occupy and plug the air passage into the collapsed lung tissue region CLT.

Figure 12A:
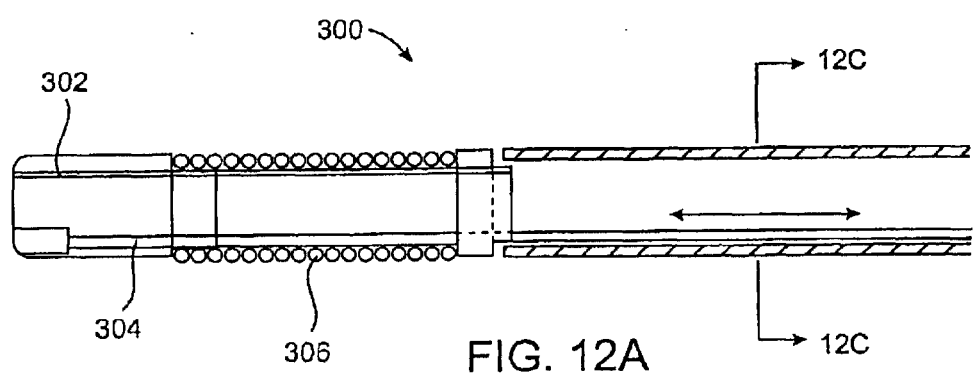
FIGS. 12A–12C illustrate a steerable imaging guidewire which may be used to facilitate positioning of the isolation/access catheter used in the methods of the present invention.
Figure 12B:
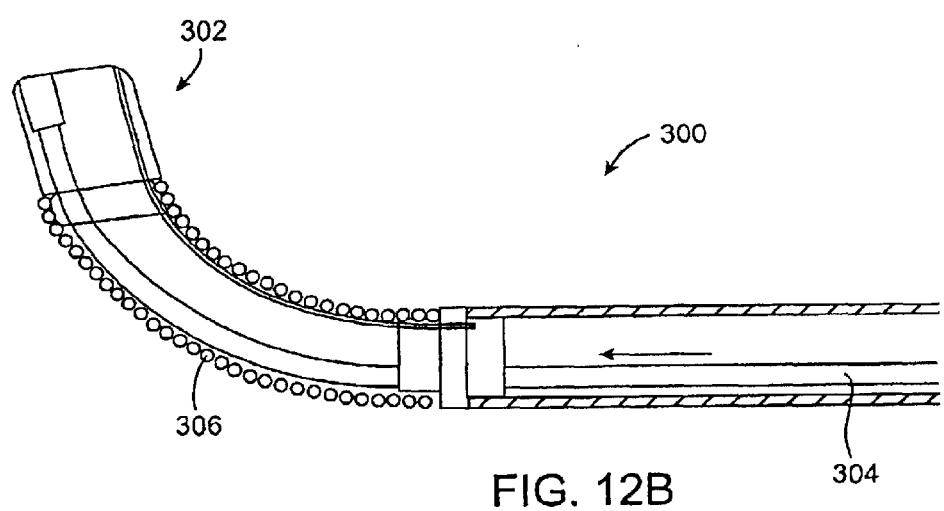
Figure 12C:
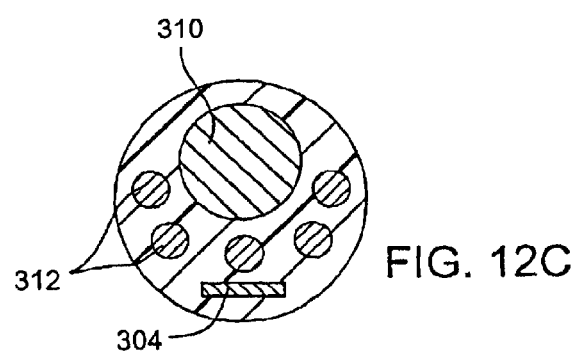

Positioning of the isolation/access catheter 10 within the lung can be performed using on-board optical imaging capability, as discussed above. Usually, positioning of a guidewire through the branching bronchus will be manipulated while viewing through the imaging components of the isolation/access catheter. In this way, the isolation/access catheter can be "inched" along by alternately advancing the guidewire and the isolation/access catheter. As an alternative to providing the isolation/access catheter with imaging, positioning could be done solely by fluoroscopy. As a further alternative, a steerable, imaging guidewire 300 (FIGS. 12A–12C) could be used. The guidewire 300 includes a deflectable tip 302 which can be deflected in a single plane using push/pull ribbon 304. Usually, the tip will comprise a spring 306 to facilitate deflection. In addition to steerability, the guidewire 300 will include an optical imaging wave guide 310 and illuminating optical fibers 312, as best seen in cross-sectional view of FIG. 12C. Thus, the guidewire 300 can be steered through the branching bronchus to reach the target tissue segment using its own in situ imaging capability. Once the guidewire 300 is in place, an isolation/access catheter can be introduced to the target lung tissue segment as well. Since the guidewire has imaging capability, the isolation/access catheter need not incorporate such imaging. This can be an advantage since it permits the access lumen to be made larger since the catheter need not carry any optical wave guides.

In addition to the methods and devices described previously, the lung sealing protocols of the present invention can be performed with a variety of two component systems comprising generally an expandable plug or barrier and an adhesive which is introduced against the expandable plug or barrier. While in many instances a single expandable plug or barrier, as described previously, may be sufficient, in other instances it may be desirable to combine such a plug/barrier with an adhesive, sealant, glue, or other similar substance which can facilitate sealing around the periphery of the plug as well as enhanced sealing across the surface of the plug itself.

Figure 14A:
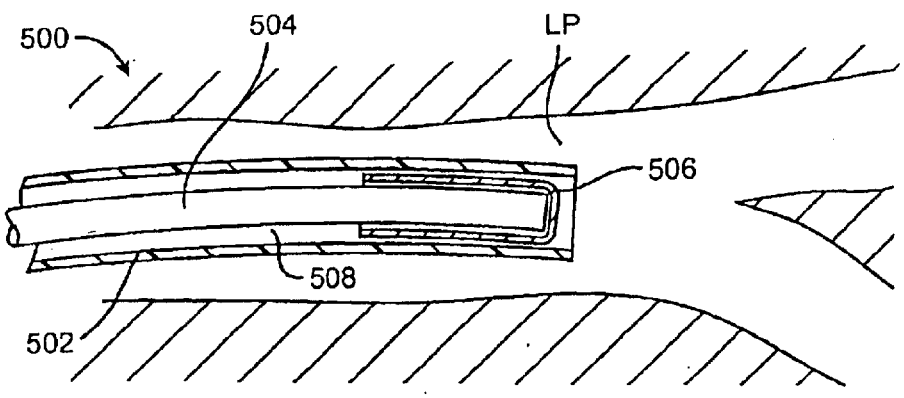
FIGS. 14A–14C illustrate the use of an alternative catheter system for implanting a mechanical plug in combination with an adhesive sealant in accordance with the principles of the methods of the present invention.
Figure 14B:
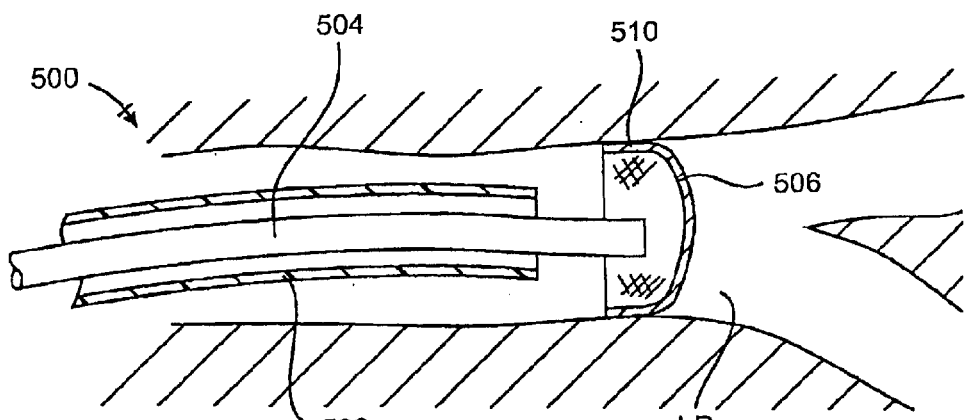
Figure 14C:
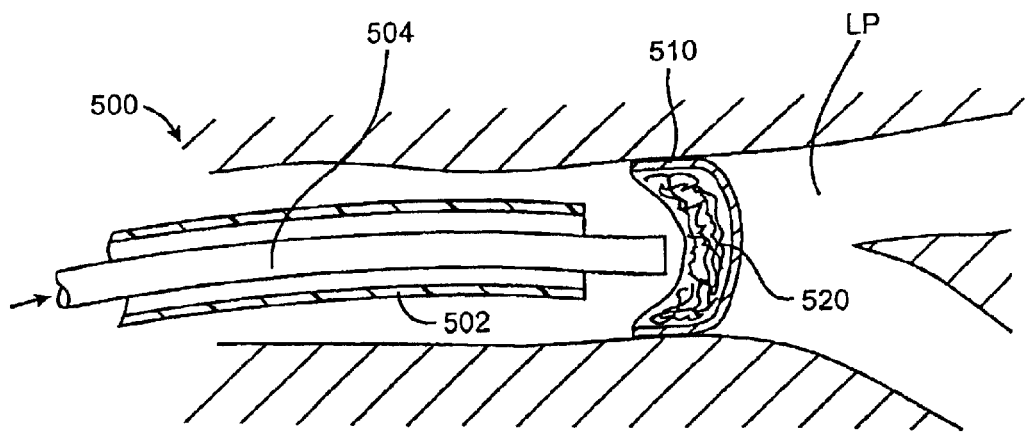

Referring now to FIGS. 14A–14C, a catheter system 500 comprising an outer sheath 502, and inner tube 504 is used to deliver an expansible barrier 506. As shown in FIG. 14A, the barrier 506 is initially contained over a distal end of the inner tube 504 and within a lumen 508 of the outer sheath 502. Barrier 506 can have a variety of forms, but will generally be formed from a resilient metal, optionally a shape memory alloy, which is configured to be released from the catheter assembly 500 and to expand across the lung passage LP, as shown in FIG. 14B. The barrier may be in the form of a mesh, grid, membrane, or other specific structures, and will have a peripheral edge 510 which is configured to engage against the wall of the lung passage LP. Optionally, the barrier 506 will have an impermeable fabric or other layer attached across its surface for inhibiting passage of air and/or contain a sealant.

While the barrier 506 could be delivered in a variety of ways, it is shown to be delivered by retracting the outer sheath 502 from over the inner tube 504 so that the barrier 506 expands radially outwardly after the sheath 502 is withdrawn. While in certain embodiments the expansible barrier 506 could be sufficient to occlude the lung passage LP, i.e., prevent the flow of gasses thereacross, it will generally be preferred to enhance occlusion by delivering an adhesive material 520, as shown in FIG. 14C. Conveniently, the adhesive 520 will be a liquid or other flowable material which can be introduced through a lumen of the inner tube 504. Suitable materials include albumin, collagen or fibrin based, synthetic or non-synthetic adhesives, preferably mixed with radiopaque tracers, such as silver nitrate, barium sulfate or any other traceable biocompatible material. The adhesive will generally be curable so that it forms a solid mass adjacent to the barrier 520, which in particular seals the peripheral portion 510 against the wall.

Figure 15A:
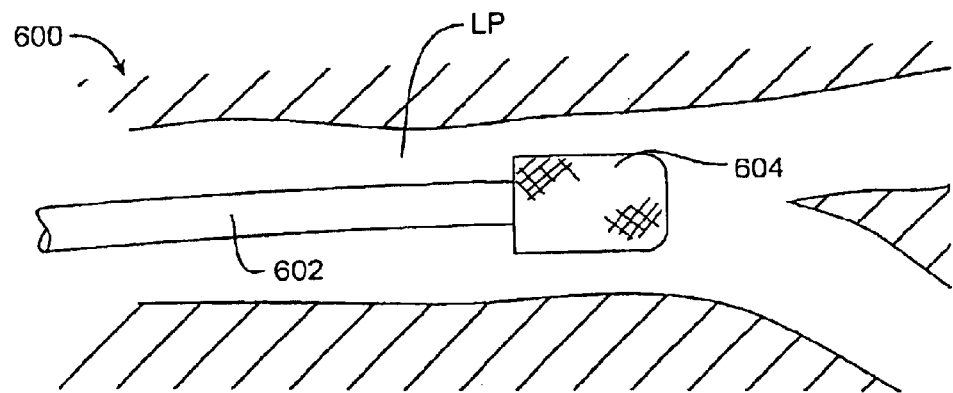
FIGS. 15A–15C illustrate a method similar to that shown in FIGS. 14A–14C, except that the mechanical plug is shown to be balloon expandable rather than self-expanding.
Figure 15B:
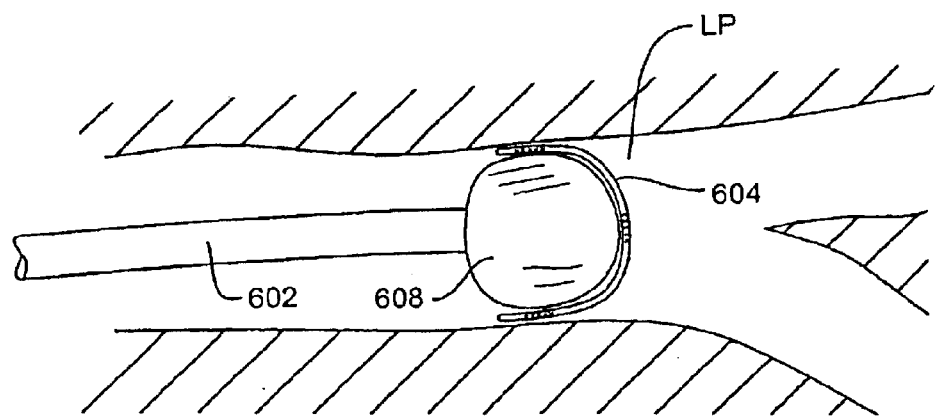
Figure 15C:
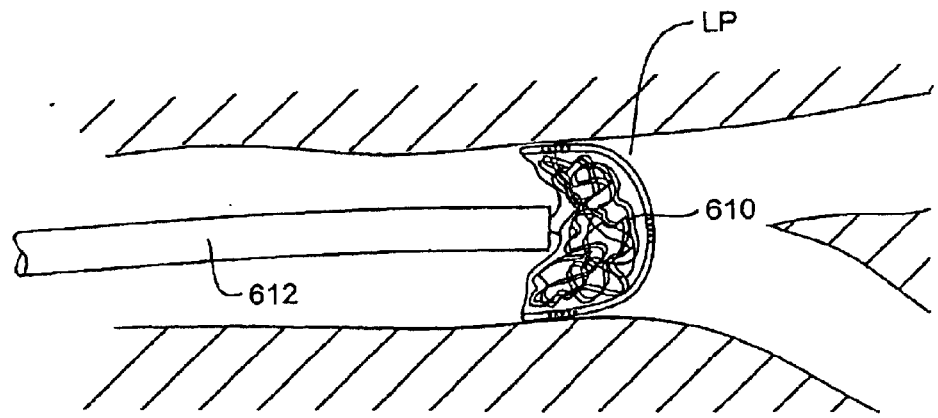

Referring now to FIGS. 15A–15C, catheter system 600 includes catheter body 602 having a balloon-expansible barrier 604 at its distal end. A balloon 608 at the distal end of catheter 602 may best be used to expand the barrier 604, as shown in FIG. 15B. The barrier 604 may be composed of a wide variety of malleable materials, such as stainless steel, and will typically be in the form of a mesh, braid, or other similar structure. Optionally, the barrier 604 may include a fabric or membrane barrier laminated thereto to enhance impermeability. Adhesive 610 is typically introduced through either the balloon catheter 602 or optionally a separate adhesive delivery catheter 612, as shown in FIG. 15C.

Figure 16A:
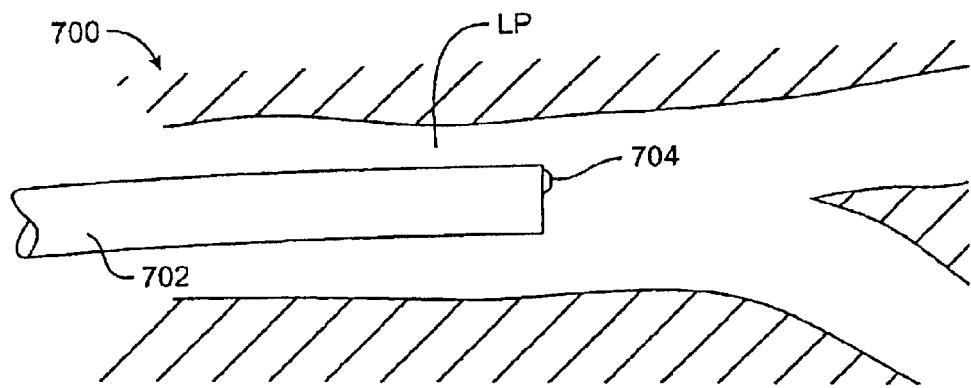
FIGS. 16A–16F illustrate yet another exemplary method according to the present invention where a swellable collagen plug is first introduced followed by introduction of an adhesive sealant adjacent to the plug.
Figure 16B:
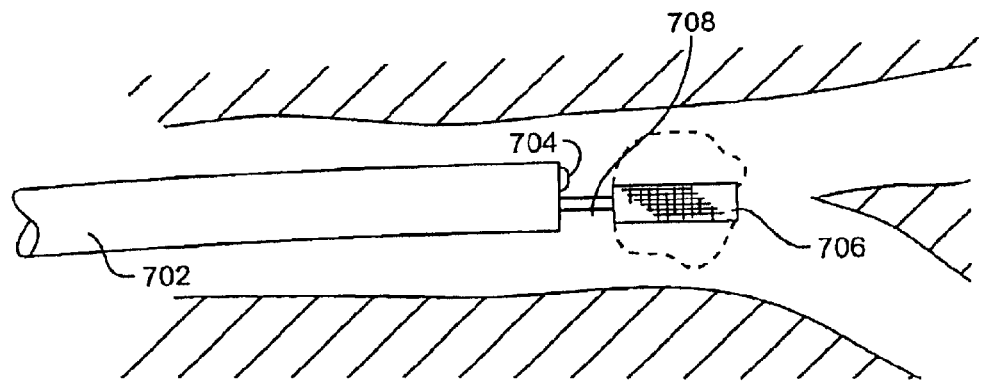
Figure 16C:
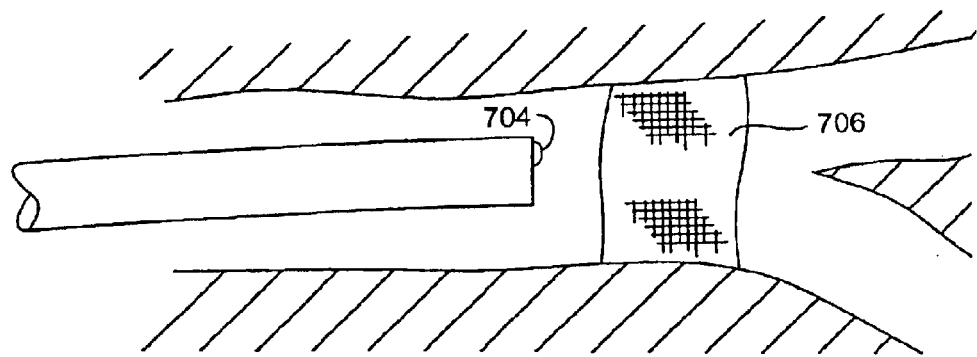
Figure 16D:
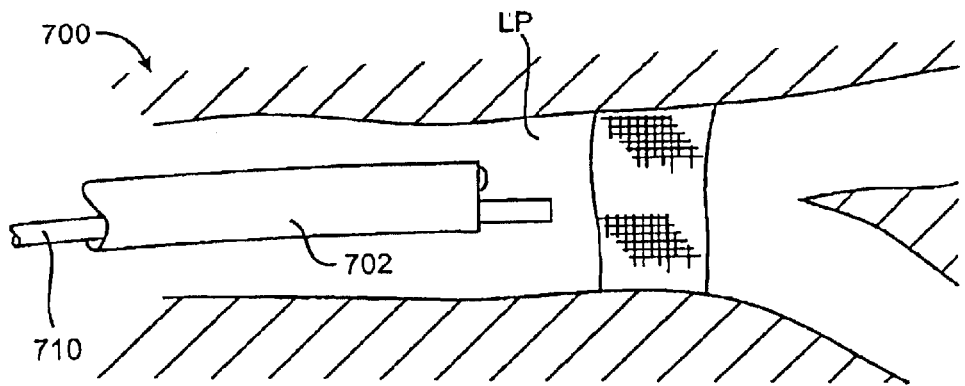
Figure 16E:
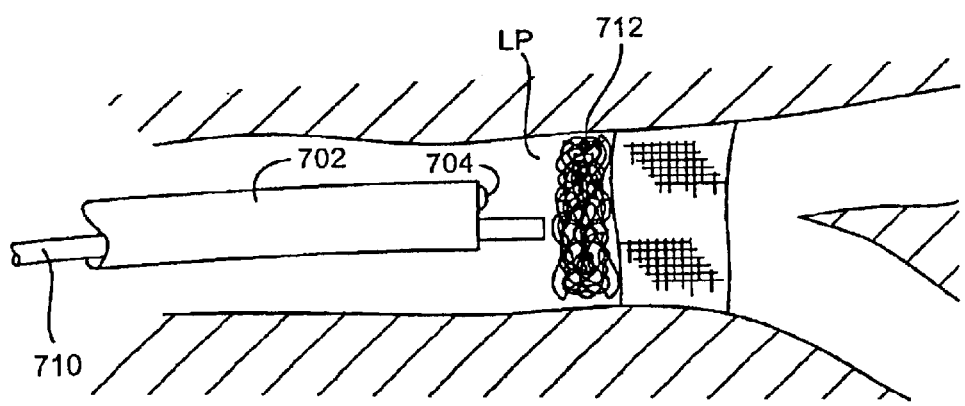
Figure 16F:
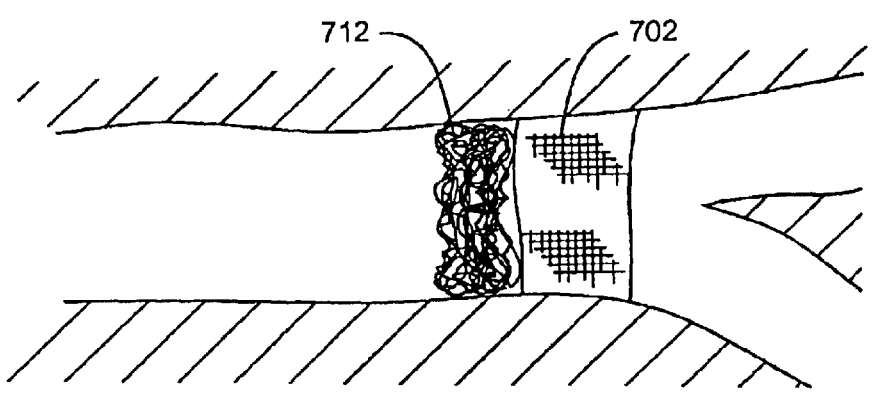

Referring now to FIGS. 16A–16E, a third approach for delivering a two-component sealing system according to the present invention will be described. A system 700 comprises a catheter 702 having an optical fiber viewing component 704 at its distal end. The catheter 702 is initially positioned in the lung passage LP at the region to be occluded. A swellable collagen or other plug is then released from the catheter 702, as shown in FIG. 16B. Preferably, the plug 706 will be advanced by a positioning wire 708 which remains attached to the plug 706 to allow positioning of the plug 706 while it is expanding. After the plug 706 is fully expanded and properly positioned, the wire 708 may be withdrawn, as shown in FIG. 16C. It will be appreciated that all of the foregoing steps are optionally accomplished while viewing with the use of the fiberoptic viewing component 704. A separate adhesive delivery tube 710 may then be introduced through the catheter 702, as shown in FIG. 16D. Adhesive 712 may then be delivered through the tube 710, again while the procedure is preferably being viewed via the optical viewing component 704. After the adhesive 712 is introduced, the catheter 762 and all associated components may be withdrawn, as shown in FIG. 16F, leaving the barrier comprising the swellable plug 702 and adhesive substance 712 in place.

Figure 13:
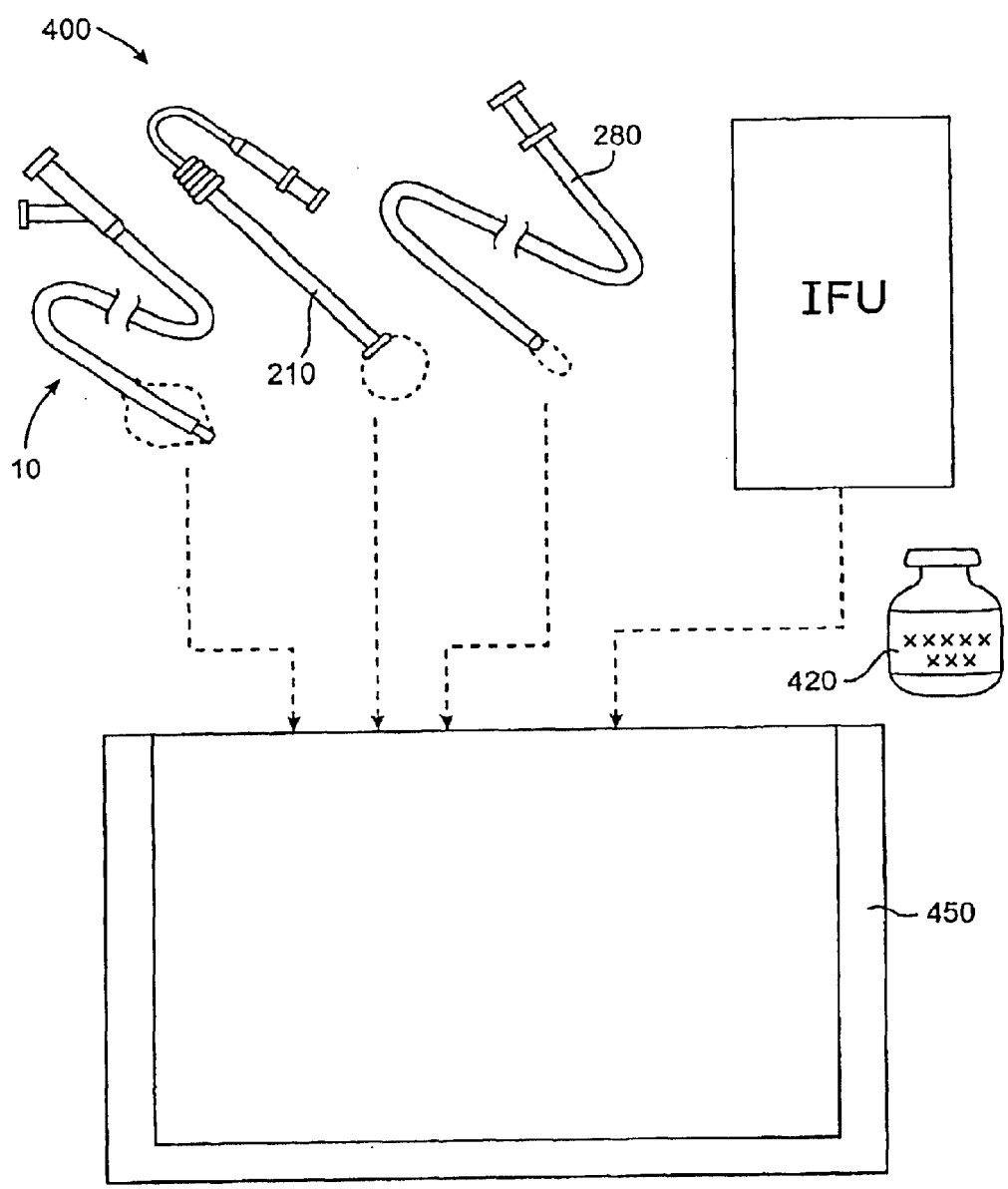
FIG. 13 illustrates a kit constructed in accordance with the principles of the present invention.

Referring now to FIG. 13, kits 400 according to the present invention comprise at least an isolation/access catheter 10 and instructions for use IFU. Optionally, the kits may further include any of the other system components described above, such as a balloon probe 210, a sealing catheter 280, a reagent container 420 (optionally including any of the dilating or mucolytic agents described above), or other components. The instructions for use IFU will set forth any of the methods as described above, and all kit components will usually be packaged together in a pouch 450 or other conventional medical device packaging. Usually, those kit components, such as isolation/access catheter 10, which will be used in performing the procedure on the patient will be sterilized and maintained sterilely within the kit. Optionally, separate pouches, bags, trays, or other packaging may be provided within a larger package, where the smaller packs may be opened separately and separately maintain the components in a sterile fashion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for lung volume reduction, said method comprising:
   isolating a lung tissue segment;
   aspirating the segment through a lung passage to cause the segment to at least partially collapse; and
   implanting a barrier formed at least in part from a metal composition which expands in situ across the lung passage.

2. A method as in claim 1, further comprising inflating the lung tissue segment to a pressure higher than its normal inflated pressure to reduce gas flow obstruction.

3. A method as in claim 2, further comprising deflating adjacent lung regions while the lung tissue segment is inflated.

4. A method as in claim 2, wherein inflating the lung tissue segment comprises positioning a catheter in an air passage leading into the segment, inflating a balloon on the catheter to seal the air passage, and introducing a gas through the catheter to inflate the segment.

5. A method as in claim 1, further comprising introducing an agent to the lung tissue segment, wherein the agent clears or dilates air passages within the segment to reduce gas flow obstructions.

6. A method as in claim 5, wherein the agent is selected from the group consisting of mucolytic agents, bronchodilators, surfactants, desiccants, solvents, necrosing agents, perfluorocarbons, and absorbents.

7. A method as in claim 5, wherein introducing the agent comprises positioning a catheter in an air passage leading to the segment and delivering the agent through the catheter to the segment.

8. A method as in claim 1, further comprising delivering mechanical energy to the lung segment to reduce gas flow obstructions.

9. A method as in claim 8, wherein the mechanical energy is vibrational energy.

10. A method as in claim 8, wherein the vibrational energy is delivered by inflating the segment with a non-compressible fluid and ultrasonically exciting the fluid to distribute ultrasonic energy throughout the segment.

11. A method as in claim 1, wherein isolating the lung tissue segment comprises positioning a catheter in an air passage leading to the lung tissue segment and inflating a balloon on the catheter to occlude the air passage.

12. A method as in claim 11, wherein aspirating comprises drawing gas and liquids present from the isolated lung segment through a lumen in the catheter while the balloon remains inflated.

13. A method as in claim 12, wherein aspirating is performed at a negative pressure in the range from 2 mmHg to 50 mmHg.

14. A method as in claim 1, wherein implanting the barrier further comprises introducing a collagen hydrogel which is not fully hydrated prior to deployment.

15. A method as in claim 1, wherein implanting a barrier further comprises introducing an adhesive in the air passage.

16. A method as in claim 15, wherein the adhesive includes a radiopaque tracer.

17. A method as in claim 1, wherein aspirating the segment is performed after implanting the barrier.

18. A method as in claim 1, wherein the barrier comprises a metal frame and an air impermeable cover.

19. A method as in claim 18, wherein the metal frame is resilient and adapted to expand upon release from constraint.

20. A method as in claim 18, wherein the metal frame is balloon expandable.

21. A method as in claim 1, further comprising inducing absorption atelectasis within the lung segment prior to aspirating the segment.

22. A method as in claim 20, wherein inducing absorption atelectasis comprises insufflating the lung segment with a high oxygen concentration gas.

23. A method as in claim 22, wherein the high oxygen concentration is at least 50% by volume.

24. A method as in claim 22, wherein the high oxygen concentration is at least 75% by volume.

25. A method as in claim 22, wherein the oxygen is substantially pure.

26. A method as in claim 22, wherein the lung is lavaged with a mixture of oxygen and a low molecular weight gas.

* * * * *